United States Patent [19]
Sidransky et al.

[11] Patent Number: 5,856,094
[45] Date of Patent: Jan. 5, 1999

[54] METHOD OF DETECTION OF NEOPLASTIC CELLS

[75] Inventors: David Sidransky; Stephen B. Baylin, both of Baltimore, Md.

[73] Assignee: The Johns Hopkins University School of Medicine, Baltimore, Md.

[21] Appl. No.: 497,535

[22] Filed: Jun. 30, 1995

Related U.S. Application Data

[63] Continuation-in-part of Ser. No. 439,962, May 12, 1995, Pat. No. 5,767,258.

[51] Int. Cl.$^6$ ...................................................... C12Q 1/68
[52] U.S. Cl. .......................... 435/6; 536/23.5; 536/24.31
[58] Field of Search ................................ 435/6; 536/23.5, 536/24.31

[56] References Cited

PUBLICATIONS

Herman, et al., *Hypermethylation–associated Inactivation Indicates a Tumor Suppressor Role for p15$^{INK4B1}$*, Cancer Research, 56:722, 1996.

Herman, et al., *Inactivation of the CDKN2/p16/MTS1 Gene is Frequently Associated with: Aberrant DNA Methylation in All Common Human Cancers*, Cancer Research, 55:4525, Oct. 15, 1995.

Merlo, et al., *A Novel p16$^{INK4A}$ Transcript*, Cancer Research, 55:2995, Jul. 15, 1995.

Shapiro, et al., *Multiple Mechanisms of p16$^{INK4A}$ Inactivation in Non–Small Cell Lung Cancer Cell Lines*, Cancer Research, 55:6200, Dec. 15, 1995.

Liggett, et al., *p16 expression is modulated by an alternative transcript (p16β) in vitro and may be a mechanism of tumor suppressor gene regulation*, Proceedings of the American Association for Cancer Research, vol. 37(#20), Mar. 1996.

Serrano et al., "*A new regulatory motif in cell–cycle control causing specific inhibition of cyclin D/CDK4*", Nature, Dec. 16, 1993, vol. 366, pp. 704–707.

Cairns et al., Cancer Research 55:224–227, Jan. 1995.

*Primary Examiner*—Scott W. Houtteman
*Attorney, Agent, or Firm*—Fish & Richardson P.C.

[57] ABSTRACT

Methylation of p16 DNA and a resultant decrease in p16 gene expression is associated with transcriptional block and is associated with a variety of neoplasms. A method for detecting a neoplasm in a subject by detecting methylation of 5'CpG islands in p16 DNA, or detecting p16 mRNA or polypeptide levels in a sample is also provided.

15 Claims, 11 Drawing Sheets

TCCCGAGGCAGTTATGTGAAATATGGCCTCGATCTTGGAGGTCCGGGTGGGAGTGGGGT 60
GGGGTGGGGGTGAAGGTGGGGGCGCGGGCGCTCAGGGAAGGCGGGTGCGCGCC 120
TGCGGGGGCGAGATGGGCAGGGGGGCGTGCGTGGGTGCCCAGTCTGCAGTTAAGGGGCAG 180
GAGTGGCGCTGCTCACCTCTGGTGCCAAAGGCGGGCCAGCGGCTGCCGAGCTCGGCCCT 240
GGAGGGCGAGAACATGGTGCGCAGGTTCTTGGTGACCCTCCCGGATTCGGGCGCGTGC 300
GGCCCGCGCGAGTGAGGGTTTCGTGGTTCACATCCCGCGCTCACGGGGAGTGGGCA 360
GCGCCAGGGGCGCCCCGCCTGTGGCCCCTCGTGCTACTGAGGAGCCAGCGTCTA 420
GGGCAGCAGCCGCTTCCTAGAAGACCAGTAGGAAAGGCCCTCGAAAAGTCCGGGGCGCA 480
CTTGTTTTGTTTGGTGTGATTCGTAAACAGATAATTCGTCTCTAGCCCATTCTAGGA 540
GGAGGAGGAGATAACCGCGGTGCTCCCATTCGGGTTACAACGACTTAGACATGTG 600
GTTCTCCAGTACCATTGAACCTGACCCTCCCTTCACACAGCCCTCAATCGTGGGAAACT 660
GAGGCGAACAGAGCTTCTAAACCCACCTCAGAAGTCAGTGAGTCCCGAATATCCTGGGTG 720
GGAATGACTAAGACACACACACACACACCCACACACACACACACACAGTAGGAAATGT 780

FIG. 1a

P16 EXON 1

<p16e1.nt

ACATTCGCTAAGTGCTCGGAGTTAATAGCACCTCCTCCGTCCGTAGTCACGGCTTCACGGCGTCCCTTCCT
GGAAAGATACACGGTCCCTCCAGAGGATTTGAGGGACAGGGTAGGAGGGGCTCTTCCGCCAGCA
CCAGAGGAAGAAAGAGGAGGGGCTGGCTGGTCACCAGAGGGTGGGGCGGACCGCGTGCGCTCG
GCGGGCTGCGGAGAGGGGGAGAGCAGGCAGCGGGCGGCGGGGAGCAGCATGGAGCCGGCGG
GGAGCAGCATGGAGCCTTCGGCTGACTGGCTGGCCACGGCCGCGGCCCCGGGTCGGGTAGAGGA
GGTGCGGGCGCTGCTGGAGGCGGGGGCGCTGCCCAACGCACCGAATAGTTACGGTCGGAGGCCG
ATCCAGGTGGGTAGAGGGTCTGCAGCGGGATGGCGGGGGCGACTCTGGAGGACGAAGTT
TGCAGGGGAATTGGAATCAGGTAGCGC

FIG. 3b

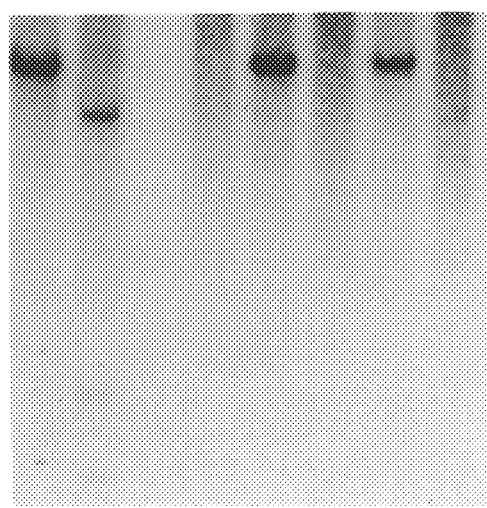
FIG. 5a
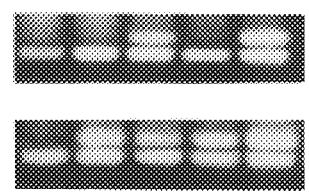
FIG. 5b
FIG. 5c
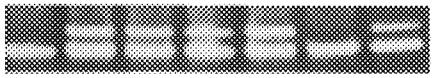
FIG. 5d

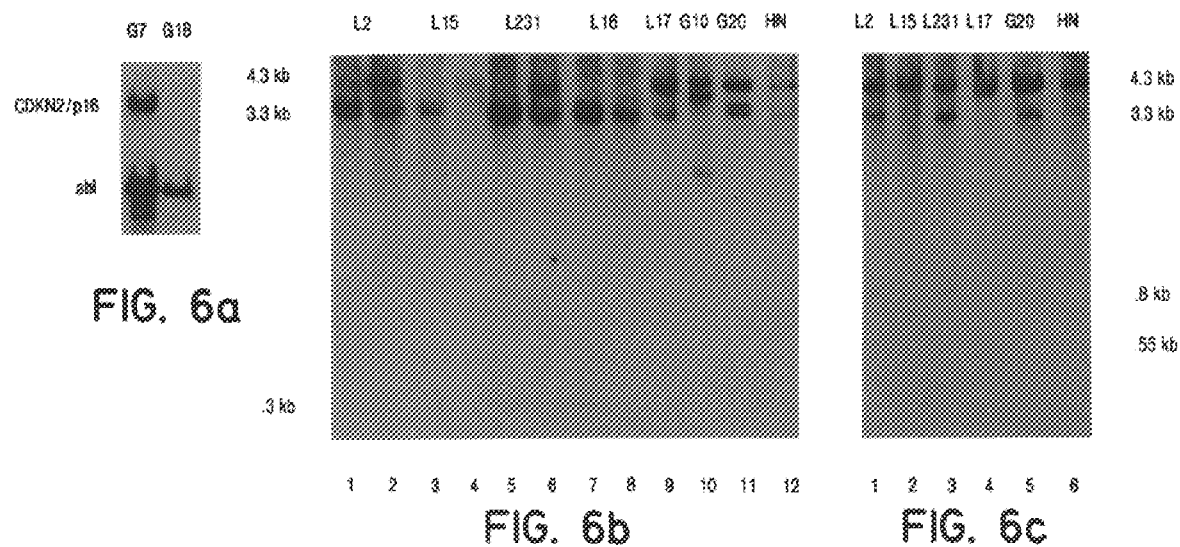

METHOD OF DETECTION OF NEOPLASTIC CELLS

This application is a continuation-in-part of U.S. Ser. No. 08/439,962, filed May 12, 1995, now U.S. Pat. No. 5,767,258.

BACKGROUND OF THE INVENTION

1. Field of the Invention

This invention relates to regulation of cell growth and proliferation and specifically to a novel cell cycle-related polynucleotide, 5'ALT, and novel polynucleotides encoding truncated cell cyclin inhibitors, p16$^{INK4A}$ and p15$^{INK4B}$. The invention also relates to the identification of neoplastic cells in a sample, by detecting p16 mRNA, polypeptide, and 5'CpG island methylation of p16DNA.

2. Description of Related Art

The growth cycle of eukaryotic cells is regulated by a family of protein kinases known as the cyclin-dependent kinases ("CDKs"). The cyclins and their associated CDKs move cells through the three phases of the growth cycle (G1, S and G2, respectively) leading to division in the mitosis phase (M). The cyclin/CDK complexes whose role in cellular proliferation has been most clearly defined to date are the cyclin D/CDK enzymes, which are believed to assist in the progression of the G1 growth cycle phase. Of these enzymes, cyclin D1 is believed to be an oncogene, whose overexpression stimulates excessive cell division through the continuous production of kinase, thus contributing to the development of cancers of, for example, the breast and esophagus. Cyclin D1 is specifically bound by CDK4 as part of a multi-protein complex that also consists of a protein known as p21 and cell nuclear antigen. Known inhibitors of such cyclin/CDK overexpression include the tumor suppressor protein p53 and the protein product of the retinoblastoma (Rb) gene. Recently, two putative inhibitors of cell cyclins, p16$^{INK4A}$ and p16$^{INK4B}$, were isolated (Serrano, et al., Nature, 366:704, 1993; Hannon, et al., Nature, 371:257, 1994, respectively). The cyclin-CDK inhibitors p16$^{INK4A}$ (CDKN2MTS-1) and p15$^{INK4B}$ (MTS-2) are inportant components of cell cycle regulation. Transition through G1 is promoted by the cyclin-dependent protein kinases CDK4 and CDK6 which phosphorylate Rb resulting release of E2F and cell cycle progression (Hunter, T. & Pines, J.,Cell 79: 573–582, 1994). In addition to more universal inhibitors (Morgan, D. O., Nature, 374:131–134, 1995), these kinases are strongly inhibited both p16$^{INK4A}$ and p15$^{INK4B}$. Isolation of the genes for these negative cell cycle regulators was quickly followed by their co-localization to chromosome 9p21, within a critical region commonly deleted in many types of human cancer (Kamb, A., et al., Science, 264:436–440, 1994; Nobori, T., et al., Nature, 368:753–756, 1994). Familial and sporadic malignant melanomas have been consistently associated with cytogenetic abnormalities of chromosome 9p21 (Fountain, et al., Proc. Natl. Acad. Sci., USA, 89:10557, 1992; Cannon-Albright, et al., Science, 258:1148, 1992) Deletions of this region are also common in gliomas (Olopade, et al., Cancer Res., 52:2523, 1992), lung cancers (Olopade, et al., Cancer Res., 53:2410, 1993), and leukemias (Olopade, et al., Genomics, 14:437, 1992). Although excellent tumor suppressor gene candidates, somatic point mutations were found to be rare in many primary human tumors with hemizygous loss of 9p21 (Cairns, et al., Science 245:415–416, 1994).

Frequent loss of heterozygosity (LOH) and homozygous deletion of chromosome 9p21 has suggested the presence of tumor suppressor genes in this region. Localization of an inhibitor of the cyckin D/cyclin dependent kinase 4 complex, now called CDKN2/p16, to 9p21, along with frequent homozygous deletions of this gene in human cancer cell lines, suggested that p16 might be the target gene (Kamb, et al, supra; Nobori, et al., supra). Since the initial reports of this homozygous deletion, numerous studies have shown varying, but in general much less frequent, abnormalities of p16 in primary tumors of these cancers. For example, although the rate of homozygous deletions ranged from 40–60% of breast cancer cell lines (Kamb, et al., supra; Xu, et al., Cancer Res., 54:5262, 1994), neither homozygous deletion or point mutations are typically observed in primary breast carcinomas. Also, certain common neoplasms, such as prostate and colon cancer, have not been found to harbor homozygous deletions in established cell lines.

In this regard, allelic loss of 9p21 has been found to occur early in the progression of at least two tumor types (Cairns, et al., Oncogene, 8:1083, 1993; van der Riet, et al., Cancer Res., 54:1156, 1994). Hemi- and homozygous losses of chromosome 9p21 are among the most common changes found in most tumor cell lines (Olopade, et al., Genomics, 14:437, 1992) and primary tumors (Merlo, et al. Cancer Res., 54:640, 1994; Migeon, et al., Genet Res., 56:91, 1990).

In eukaryotic cells, methylation of cytosine residues that are immediately 5' to a guanosine, occurs predominantly in CG poor regions (Bird, A., Nature, 321:209, 1986). In contrast, discrete regions of CG dinucleotides called CpG islands remain unmethylated in normal cells, except during X-chromosome inactivation (Migeon, et al., supra) and parental specific imprinting (Li, et al., Nature, 366:362, 1993) where methylation of 5' regulatory regions can lead to transcriptional repression. De novo methylation of the Rb gene has been demonstrated in a small fraction of retinoblastomas (Sakai, et al., Am. J Hum. Genet., 48:880, 1991), and recently, a more detailed analysis of the VHL gene showed aberrant methylation in a subset of sporadic renal cell carcinomas (Latif, et al., Cancer Res., 52:1451, 1992). Expression of a tumor suppressor gene can also be abolished by de novo DNA methylation of a normally unmethylated 5'CpG island (Issa, et al., Nature Genet., 7:536, 1994, Herman, et al., Proc. Natl. Acad Sci., U.S.A., 91:9700, 1994).

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

SUMMARY OF THE INVENTION

The present invention provides novel cell cycle regulatory polynucleotides and the polypeptides they encode. The polynucleotide transcripts identified herein are a product of alternative splicing mRNA of the cyclin/CDK inhibitors, p16$^{INK4A}$ and p15$^{INK4B}$, and a novel 5' nucleotide sequence referred to herein as "5'ALT".

p16$^{INK4A}$ and p15$^{INK4B}$ colocalize to chromosome 9p21, which has been identified as a region having homozygous deletions in many tumors. 5'ALT is shown in the present invention to also reside on chromosome 9p21, just 5' of exon 2 of p15$^{INK4B}$, and about 30 kb upstream from p16$^{INK4A}$ (see FIG. 2).

In one embodiment, the present invention provides an isolated polynucleotide having the nucleotide sequence of SEQ ID NO:1, which includes the 5'ALT sequence found in the novel transcripts described herein as well as an upstream region which is GT-rich and a downstream element which contains a highly polymorphic CA stretch.

In a second embodiment, the invention provides a polynucleotide having a 5'ALT polynucleotide operatively linked to exon 2 and exon 3 of p16$^{INK4A}$ and the polypeptide encoded by the polynucleotide. In yet another embodiment, the invention provides a polynucleotide having a 5'ALT polynucleotide operatively linked to exon 2 of p15$^{INK4B}$ and the polypeptide encoded by the polynucleotide.

The identification of these novel transcripts which are associated with normal growth control and regulation of cellular proliferation provides a means for the development of more accurate diagnostic, prognostic and therapeutic regimes for disorders associated with control of cell cycle progression and cell differentiation and the loss of such control.

The invention also provides a method for detection of a cell proliferative disorder, e.g., a neoplasm, in a tissue of a subject, the method comprising contacting a target cellular component of the tissue with a reagent which detects alterations in p16, such as p16 methylation. Preferably, the method of invention utilizes a methylation sensitive restriction endonuclease in order to detect p16 methylation.

BRIEF DESCRIPTION OF THE DRAWINGS

FIG. 1a shows the polynucleotide sequence of 5'ALT (SEQ ID NO:1). The 268 bp fragment of 5'ALT contained in the p16$^{INK4A}$ and p15$^{INK4B}$ transcripts is underlined. A putative GT promoter element (bold, double-underlined) and the primer used for the primer extension assay (bold, italics, underlined) are shown. The highly polymorphic (CA)$_n$ repeat is shown on the last line.

FIG. 3b shows the nucleotide sequence of the first exon of p16.

FIGS. 5a–d show re-expression of transcriptionally silenced p16 after treatment with 5'-deoxyazacytidine in cancer cell lines.

FIGS. 6a–c show homozygous deletions and de novo methylation of the 5'CpG. island of p16 in human primary tumors.

DETAILED DESCRIPTION OF THE INVENTION

Figure 1B:
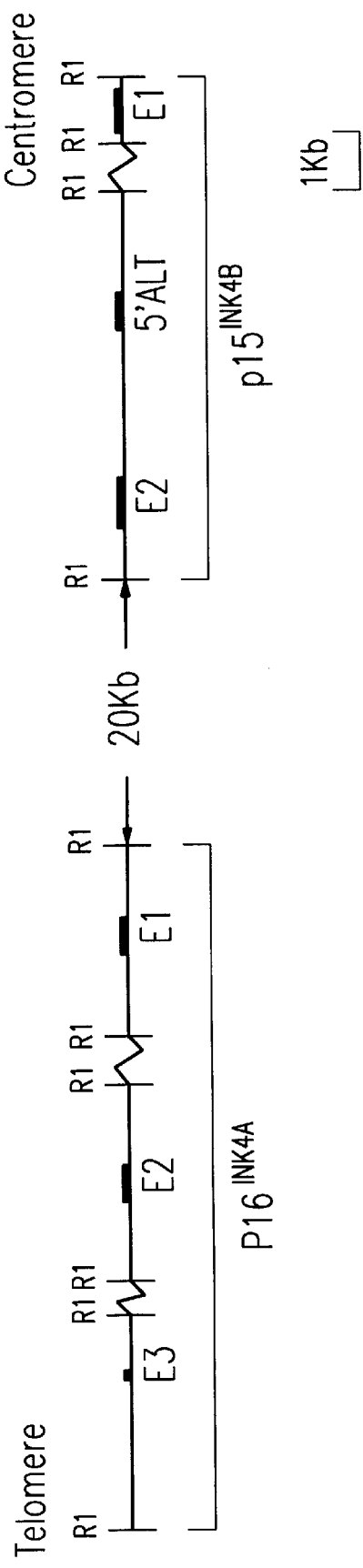
FIG. 1b shows the genomic organization of 5'ALT. Coding exons for p15$^{INK4B}$ and p16$^{INK4A}$ are designated by black boxes. E1=exon 1, E2=exon 2 and E3=exon 3. 5'ALT is located between exon 1 and 2 of p15$^{INK4B}$ and approximately 30Kb upstreat of exon 1 of p16$^{INK4A}$.

The present invention provides novel p16$^{INK4A}$ and p15$^{INK4B}$ polynucleotides hereafter referred to as p16 or p15, and polypeptides which are identified by a novel upstream polynucleotide sequence called "5'ALT". These novel alternative p16 and p15 transcripts generated from the novel 5'ALT sequence are involved in the complex regulation of these critical cell cycle genes.

Most nuclear messenger RNA precursors (pre-mRNA) in higher eukaryotes contain multiple introns which are precisely excised by RNA splicing. Several pre-mRNAs are attentively spliced in different cell types or at different times during development. Alternative splicing can result in the production of more than one different protein from a single pre-mRNA. One mode of splicing can generate a mRNA that lacks an open translational reading frame, and alternative splicing of the same pre-mRNA yields a functional protein. Alternative splicing has been described in the regulatory hierarchy of sex determination of Drosophila and in many examples of tissue-specific gene expression. The novel alternative mRNAs of the invention, and the truncated proteins encoded by these transcripts, are produced as a result of alternative splicing, rather than gene rearrangement.

Initial studies in the present invention revealed that de novo methylation of a CpG island that extends into exon 1 of p16 in cell lines and primary tumors is precisely associated with transcriptional block of full length p16. Reversal of methylation with 5'-azacytidine resulted in reexpression of p16 message. However, methylated cell lines always expressed an abundant, shortened p16 transcript entirely devoid of exon 1 coding sequences (see EXAMPLE 5).

The present invention shows that hypermethylation of the 5'CpG island of CDKN2/p16 is frequent in cell lines and primary tumors of other common human neoplasms. Furthermore, inactivation through DNA methylation can occur not only in neoplasms where homozygous deletion is frequent (breast, renal cell) but also in those which are not commonly associated with loss of p16 through homozygous deletion (colon and prostate). The findings provided in the EXAMPLES herein show that hypermethylation of the p16 gene promoter region is a common abnormality of p16 in human cancers, e.g., neoplasms.

In a first embodiment, the present invention provides an isolated polynucleotide (5'ALT) having the nucleotide sequence of SEQ ID NO:1, shown in FIG. 1a, and sequences substantially complementary thereto. The invention also provides a polynucleotide having the nucleotide sequence of SEQ ID NO:1, in operative linkage with exons 2 and 3 of p16 cyclin CDK inhibitor and sequences substantially complementary thereto, as well as a polynucleotide having the nucleotide sequence of SEQ ID NO:1, in operative linkage with exon 2 of p15 cyclin CDK inhibitor and sequences substantially complementary thereto. The term "operative linkage" refers to the organization of the nucleotide sequence such that the regulatory elements and the coding sequences are in functional linkage. The term "isolated" refers to a polynucleotide substantially free of other polynucleotides, proteins, lipids, carbohydrates or other materials with which it is naturally associated.

These polynucleotides include DNA, cDNA and RNA sequences which encode either all or a portion of 5'ALT or 5'ALT in operative linkage with p16 or p15. It is understood that all polynucleotides encoding all or a portion of 5'ALT or the p16 or p15 novel transcripts are also included herein, as long as they encode a polypeptide with the corresponding activity. Such polynucleotides include naturally occuring, synthetic, and intentionally manipulated polynucleotides. For example, 5'ALT or 5'ALT-p16 or -p15 polynucleotide may be subjected to site-directed mutagenesis. The polynucleotide sequence for 5'ALT or 5'ALT-p16 or -p15 also includes complementary, or antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of 5'ALT or 5'ALT-p16 or -p15 polypeptide encoded by the nucleotide sequence is functionally unchanged.

Specifically disclosed herein is a DNA sequence contain the human 5'ALT gene. The sequence contains an open reading frame (ORF) encoding 268 base pair transcribed product. Upstream of the ORF is a GT rich region which likely contains a GT promoter element. Downstream, at the 3' end of the ORF is a highly polymorphic $(CA)_n$ stretch which can serve as a polymorphic marker. This novel 5'ALT gene was localized to chromosome 9p21 and therefore is useful as a probe for identification of this chromosomal region, which is often deleted in human cancers. As shown in the EXAMPLES, the 5'ALT-p16 product migrates at about 9–10 kD as determined by reducing SDS-PAGE. While not wanting to be bound by a particular theory, it appears that the 5'ALT-p16 expression product is translated in frame from the third methionine of p16, just inside exon 2 and a consensus Kozak sequence (consensus ribosome binding site, TGGCCATGG; Kozak, *Nucleic Acids Res.,* 15:8125, 1987). Preferably, the human 5'ALT or 5'ALT-p16 or -p15 nucleotide sequence is the sequence of SEQ ID NO:1 including exon 2 and 3 of p16 (Serrano, et al, supra) or exon 2 of p15 (Hannon, et al., supra). The polynucleotide encoding 5'ALT or 5'ALT-p16 or -p15 includes SEQ ID NO:1 as well as nucleic acid sequences complementary to SEQ ID NO:1 and to 5'ALT-p16 or -p 15. A complementary sequence may include an antisense nucleotide. When the sequence is RNA, the deoxynucleotides A, G, C, and T of SEQ ID NO:1 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the truncated proteins encoded by the polynucleotides of the invention under physiological conditions. Specifically, the fragments should hybridize to DNA encoding 5'ALT or 5'ALT-p16 or -p15 protein under stringent conditions.

The present invention also includes polypeptides encoded by the 5'ALT or 5'ALT-p16 or p15 polynucleotides of the invention. Such polypeptides are substantially pure. As used herein, the term "substantially pure" refers to a protein which is free of other proteins, lipids carbohydrates or other materials with which it is naturally associated. One skilled in the art can purify 5'ALT or 5'ALT-p16 or p15 polypeptides using standard techniques for protein purification. For example, the substantially pure 5'ALT-p16 polypeptide will yield a single major band of approximately 9–10 kD on a non-reducing polyacrylamide gel. The purity of the 5'ALT or 5'ALT-p16 or -p15 polypeptides can also be determined by amino-terminal amino acid sequence analysis. 5'ALT or 5'ALT-p16 or -p15 polypeptides include functional fragments of the polypeptide, as long as the activity of remains. Smaller peptides containing the biological activity of 5'ALT or 5'ALT-p16 or -p15 are included in the invention.

Minor modifications of the 5'ALT or 5'ALT-p16 or -p15 primary amino acid sequence may result in proteins which have substantially equivalent activity as compared to the 5'ALT or 5'ALT-p16 or -p15 polypeptide described herein. Such modifications may be deliberate, as by site-directed mutagenesis, or may be spontaneous. All of the polypeptides produced by these modifications are included herein as long as the biological activity of 5'ALT or 5'ALT-p16 or -p15 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for 5'ALT or 5'ALT-p16 or -p15 biological activity.

The nucleotide sequence encoding the 5'ALT or 5'ALT-p16 or -p15 polypeptide of the invention includes the polypeptides encoded by the disclosed sequence (SEQ ID NO:1) in the presence or absence of exons 2 and 3 of p16, or exon 2 of p15, and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to:1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the 5'ALT or 5'ALT-p16 or -p15 polynucleotide of the invention is derived from a mammalian organics and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al, Nucl. Acid Res., 9:879, 1981; Maniatis, et al, *Molecular Cloning: A Laboratory Manual,* Cold Spring Harbor, N.Y. 1989).

The development of specific DNA sequences encoding 5'ALT or 5'ALT-p16 or -p15 can also be obtained by:1) isolation of double-stranded DNA sequence from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse tanscription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for 5'ALT or 5'ALT-p16 or -p15 peptides having at least one epitope, using antibodies specific for 5'ALT or 5'ALT-p16 or -p15. Such antibodies can be either polyclonally or monoclonally derived and used to detect expression product indicative of the presence of 5'ALT or 5'ALT-p16 or -p15 cDNA.

The primers used in the invention for detection or isolation of the novel 5'ALT gene, embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words; the primers should have sufficient complementarity with the 5' and 3' flanking sequences to hybridize therewith and permit amplification of the genomic locus.

Oligonucleotide primers of the invention are employed in the amplification process which is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the target locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from an organism found in a body sample, such as blood, urine, cerebrospinal fluid, tissue material and the like by a variety of techniques such as that described by Maniatis, et al. (*Molecular Cloning. A Laboratory Manual*, Cold Spring Harbor, N.Y., pp 280, 281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (*Ann. Rev. Genetics,* 16:405–437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase 1, T4 DNA polymerase, other available DNA polymerases, polymerase muteins, reverse transcriptase, and other enzymnes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid sand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The amplified product may be detected by analyzing it by Southern blots without using radioactive probes. In such a process, for example, a small sample of DNA containing a very low level of the nucleic acid sequence of the locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably lalabeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al, *Bio/Technology,* 3:1008–1012, 1985), allele-specific oligonucleotide (ASO) probe analysis (Conner, et al., *Proc. Natl. Acad Sci. USA,* 80:278, 1983), oligonucleotide ligation assays (OLAs) (Landegren, et al., *Science,* 241:1077, 1988), and the like. Molecular techniques for DNA analysis have been reviewed (Landegren, et al, *Science,* 242:229–237, 1988).

Preferably, the method of amplifying is by PCR, as described herein and as is commonly used by those of ordinary skill in the art. Alternative methods of amplification have been described and can also be employed as long as the 5'ALT locus amplified by PCR using the primers of the invention is similarly amplified by the alternative means. Such alternative amplification systems include self-sustained sequence replication, 3SR, which begins with a short sequence of RNA of interest and a T7 promoter. Reverse transcriptase copies the RNA into cDNA and degrades the RNA, followed by reverse transcriptase polymerizing a second strand of DNA. Another method nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ -fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair. Nucleic acid amplification by strand displacement activation (SDA) utilizes a short primer containing a recognition site for HincII with a short overhang on the 5' end which binds to target DNA. A DNA polymerase fills in the part of the primer opposite the overhang with sulfur-containing adenine analogs. HincII is added but only cut the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Although PCR is the preferred method of amplificaton of the invention, these other methods can also be used to amplify the 5'ALT locus as described in the present invention.

DNA sequences encoding 5'ALT or 5'ALT-p16 or -p15 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the 5'ALT or 5'ALT-p16 or -p15 polynucleotide sequences may be inserted into a recombinant expression vector. The term "recombinant expression vector" refers to a plasmid, virus or other vehicle known in the art that has been manipulated by insertion or incorporation of the 5'ALT or 5'ALT-p16 or -p15 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding 5'ALT or 5'ALT-p16 or -p15 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as micro-injection, electroporation, insertion of a plasmid encased in liposomes, or virus vectors may be used. Eukaryotic cells can also be cotransformed with DNA sequences encoding the 5'ALT or 5'ALT-p16 or -p15 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The 5'ALT or 5'ALT-p16 or -p15 polypeptides of the invention can also be used to produce antibodies which are immunoreactive or bind to epitopes of the 5'ALT or 5'ALT-p16 or -p15 polypeptides. While antibodies to p16 exon 2 and/or exon 3 or p15, exon 2, may be useful for production of antibodies, it may be desirable to utilize the truncated proteins to produce novel antibodies. While not wanting to be bound by a particular theory, the truncated protein may form additional conformational epitopes which are not present in wild-type p16 or p15 polypeptide, therefore, 5'ALT-p16 or -p15'ALT-specific antibodies are produced.

Antibody which consists essentially of pooled monoclonal antibodies with different epitopic specificities, as well as distinct monoclonal antibody preparations are provided.

Monoclonal antibodies are made from antigen containing fragments of the protein by methods well known in the art (Kohler, et al., *Nature,* 256:495, 1975; *Current Protocols in Molecular Biology,* Ausubel, et al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the 5'ALT or 5'ALT-p16 or -p15 polypeptide of the invention can be prepared using an intact polypeptide or fragments containing small peptides of interest as the immunizing antigen. The polypeptide or a peptide used to immunize an animal can be derived from translated cDNA (see for example, EXAMPLE 4) or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1994, incorporated herein by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first mono-clonal antibody.

The present invention provides a method of treating a disorder associated with expression of 5'ALT or 5'ALT-p16 or -p15 polynucleotide(s), comprising contacting the cell having or suspected of having the disorder with a reagent which modulates 5'ALT or 5'ALT-p16 or -p15. The term "cell-proliferative disorder" denotes malignant as well as non-malignant cell populations which often appear to differ from the surrounding tissue both morphologically and genotypically. Malignant cells (i.e. cancer) develop as a result of a multistep process. Such disorders may be associated, for example, with abnormal expression of 5'ALT or 5'ALT-p16 or -p15. "Abnormal expression" encompasses increased, decreased or absent levels of expression of 5'ALT or 5'ALT-p16 or -p15, as well as expression of a mutant form of 5'ALT or 5'ALT-p16 or -p15 such that the normal function of 5'ALT or 5'ALT-p16 or -p15 is altered. Abnormal expression also includes inappropriate expression of 5'ALT or 5'ALT-p16 or -p15 during the cell cycle or in an incorrect cell type. The 5'ALT or 5'ALT-p16 or -p15 polynucleotide in the form of an antisense polynucleotide is useful in treating malignancies of the various organ systems, for example, those of epithelioid origin (e.g., lung, breast). Essentially, any disorder which is etiologically linked to altered expression of 5'ALT or 5'ALT-p16 or -p15 could be considered susceptible to treatment with a reagent of the invention which modulates mcl-1 expression. The term "modulate" envisions the suppression of expression of 5'ALT or 5'ALT-p16 or p15when it is over-expressed, or augmentation of 5'ALT or 5'ALT-p16 or p15expression when it is under-expressed or when the 5'ALT or 5'ALT-p16 or -p15 expressed is a mutant form of the polypeptide. When a cell proliferative disorder is associated with 5'ALT or 5'ALT-p16 or -p15 overexpression, such suppressive reagents as antisense polynucleotide sequence or 5'ALT or 5'ALT-p16 or -p15 binding antibody can be introduced to a cell. In addition, polynucleotides encoding p16 or p15 can be introduced into the cell to regulate cell prolferation. Alternatively, when a cell proliferative disorder is associated with underexpression or no expression, or expression of a mutant 5'ALT or 5'ALT-p16 or -p15polypeptide, a sense polynucleotide sequence (the DNA coding strand) or 5'ALT or 5'ALT-p16 or -p15 polypeptide can be introduced into the cell.

The invention provides a method for detecting a cell expressing 5'ALT or 5'ALT-p16 or -p15or a cell proliferative disorder associated with 5'ALT or 5'ALT-p16 or -p15comprising contacting a cell suspected of expressing 5'ALT or 5'ALT-p16or -p15 or having a 5'ALT or 5'ALT-p16 or -p15associated disorder, with a reagent which binds to the component. The cell component can be nucleic acid, such as DNA or RNA, or protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation. Such analyses include delection analysis for loss of a region of 9p21.

The 5'ALT or 5'ALT-p16or -p15 polynucleotide that is an antisense molecule is useful in treating malignancies of the various organ systems, particularly, for example, cells in the central nervous system, including neural, lung, ovary, uterus, breast, head and neck, liver, pancreas tissue, etc. Essentially, any disorder which is etiologically linked to altered expression of 5'ALT or 5'ALT-p16 or -p15 or expression of an altered gene product could be considered susceptible to treatment with a 5'ALT or 5'ALT -p16 or -p15 modulating reagent. One such disorder is a malignant cell proliferative disorder, for example.

For purposes of the invention, an antibody or nucleic acid probe specific for 5'ALT or 5'ALT-p16 or -p15 may be used to detect and/or to bind to 5'ALT or 5'ALT-p16 or -p15 polypeptide (using antibody) or polynucleotide (using nucleic acid probe) in biological fluids or tissues. Any sample containing a detectable amount of 5'ALT or 5'ALT-p16 or -p15 can be used. A sample can be a liquid such as urine, saliva, cerebrospinal fluids blood, serum and the like, a cytological sample, a tumor, or sample thereof, or a solid or semi-solid such as tissues, feces, and the like, or, alternatively, a solid tissue such as those commonly used in histological diagnosis.

The invention provides a method for detecting a cell proliferative disorder which comprises contacting an anti-5'ALT or 5'ALT-p16 or -p15 antibody or nucleic acid probe with a cell suspected of having a 5'ALT or 5'ALT-p16 or -p15 associated disorder and detecting binding to the antibody or nucleic acid probe. The antibody reactive with 5'ALT or 5'ALT-p16 or -p15 or the nucleic acid probe is preferably labeled with a compound which allows detection and quantitation of binding to 5'ALT or 5'ALT-p16 or -p15. Any specimen containing a detectable amount of antigen or polynucleotide can be used. The level of 5'ALT or 5'ALT-p16 or -p15 in the suspect cell can be compared with the level in a normal cell or the nature of the transcript or gene product can be compared with a normal cell, in order to determine whether the subject has a 5'ALT or 5'ALT-p16 or -p15-associated cell proliferative disorder. Preferably the subject is human.

When the cell component is nucleic acid, it may be necessary to amplify the nucleic acid prior to binding with an 5'ALT or 5'ALT-p16 or -p15 specific probe. Preferably, polymerase chain reaction (PCR) is used, however, other nucleic acid amplification procedures such as ligase chain reaction (LCR), ligated activated transcription (LAT), QB replicase, and nucleic acid sequence-based amplification (NASBA) may be used.

The present invention identifies a nucleotide sequence that can be expressed in an altered manner as compared to expression in a normal cell, therefore it is possible to design appropriate therapeutic or diagnostic techniques directed to this sequence. Detection of elevated levels of 5'ALT or 5'ALT-p16 or -p15 expression is accomplished by hybridization of nucleic acids isolated from a cell suspected of having an 5'ALT or 5'ALT-p16or -p15 associated proliferative disorder with an 5'ALT or 5'ALT-p16 or -p15 polynucleotide of the invention. Techniques commonly used in the art, for example, Northern Blot analysis, PCR, or RNase protection assays, are utilized to quantitate expression of 5'ALT or 5'ALT-p16 or -p15. Other standard nucleic acid detection techniques will be known to those of skill in the art.

Treatment of an 5'ALT or 5'ALT-p16 or -p15 associated cell proliferative disorder includes modulation of 5'ALT or 5'ALT-p16 or -p15 gene expression and 5'ALT or 5'ALT-p16 or -p15 activity. The term "modulate" envisions the suppression of expression of 5'ALT or 5'ALT-p16 or -p15 when it is over-expressed, or augmentation of 5'ALT or 5'ALT-p16 or -p15 expression when it is under-expressed. When a cell-proliferative disorder is associated with the expression of 5'ALT or 5'ALT-p16 or -p15, agents which induce reexpression of p15 or p16 or nucleic acid sequences that interfere with 5'ALT or 5'ALT-p16 or -p15 expression at the translational level can be used. For example, when the disorder is associated with 5'ALT expression or increased methylation resulting in decreased transcription, such methylation suppressive agents as 5-deoxyazacytidine can be introduced into a cell. Other similar agents will be known to those of skill in the art. The nucleic acid approach utilizes, for example, antisense nucleic acid, ribozymes, or triplex agents to block transcription or translation of a specific 5'ALT or 5'ALT-p16 or -p15 mRNA, either by masking that mRNA with an antisense nucleic acid or triplex agent, or by cleaving it with a ribozyme. Such disorders include neurodegenerative diseases, for example.

Antisense nucleic acids are DNA or RNA molecules that are complementary to at least a portion of a specific mRNA molecule (Weintraub, *Scientific American,* 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target 5'ALT or 5'ALT-p16 or -p15 -producing cell. The use of antisense methods to inhibit the in vitro translation of genes is well known in the art (Marcus-Sakura, *Anal. Biochem.,* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1 (3):227, 1991; Helene, C., *Anticancer Drug Design,* 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med.Assn,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Treatment of an 5'ALT or 5'ALT-p16 or -p15 associated cell proliferative disorder also includes modulation of 5'ALT or 5'ALT-p16 or -p15 gene expression and 5'ALT or 5'ALT-p16 or -p15 activity by increasing or decreasing the activity or expression from the GT-rich promoter region of 5'ALT. For example, antisense or other nucleic agents are useful for blocking the promoter region, thereby inhibiting expression. Those of skill in the art will know other agents which are useful for increasing or decreasing expression from a promoter region.

The present invention also provides gene therapy for the treatment of cell proliferative or immunologic disorders which are mediated by 5'ALT or 5'ALT-p16 or -p15 protein. Such therapy would achieve its therapeutic effect by introduction of the 5'ALT or 5'ALT-p16 or -p15 antisense polynucleotide into cells having the proliferative disorder. Alternatively, it may be desirable to introduce polynucleotides encoding full length p16 or -p15 into cells. Delivery of antisense 5'ALT or 5'ALT-p16 or -p15 polynucleotide or -p16 or -p15 polynucleotide, can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to; Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a 5'ALT or 5'ALT-p16 or -p15 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the 5'ALT or 5'ALT -p16 or -p15 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA 12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for 5'ALT or 5'ALT-p16 or -p15 antisense polynucleotides or p16 or p15 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these imuunoassays can be detectably labeled in various ways. Examples of types of immunoassays which can utilize antibodies of the invention are competitive and non-competitive immunoassays in either a direct or indirect format. Examples of such irnmunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dimitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies or polynucleotides of the invention can be used in vitro and in vivo to monitor the course of amelioration of a 5'ALT or 5'ALT-p16 or -p15 -associated disease in a subject. Thus for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the 5'ALT or 5'ALT-p16 or -p15 -associated disease is effective. The term "ameliorate" denotes a lessening of the detrimental effect of the 5'ALT or 5'ALT-p16 or -p15 -associated disease in the subject receiving therapy.

In another embodiment, the invention provides a method for detecting a cell proliferative disorder, or neoplasm, in the tissue or other sample of a subject comprising contacting a cellular component with a reagent which detects an alteration in p16. As used herein, the term "alteration" refers to a change in the p16 gene from the normal gene such that gene expression is either increased or decreased. Typically, as used herein, gene expression is decreased. As shown in the present invention, methylation of 5'CpG islands in p16 DNA results in transcriptional block of p16. Therefore, detection of p16 expression can be utilized to detect such a block. For example, a methylation sensitive restriction endonuclease can be utilized to identify hypermethylated p16 DNA. In addition, decreased p16 mRNA and p16 protein can be detected by contacting a nucleic acid or protein samples from a suspected tissue with a p16-specific nucleic acid probe or antibody, respectively, as described herein for detection of 5'ALT, and comparing the levels of p16 message or protein with that of normal tissue. Methods for analysis of RNA and protein levels will be known to those of skill in the art; illustrative examples are described herein at EXAMPLES 5–11. In addition, other methods using immunohistochemical techniques and fluorescent in situ hybridization (FISH) and the like can be utilized to detect an alteration in p16.

The tissue sample used for detection of p16 may be from any source of the body of the subject, for example, from prostate, breast, colon, lung and renal tissue. Examples of methylation sensitive restriction endonucleases which can be used to detect 5'CpG methylation of p16 DNA include SmaI, SacII, EagI, MspI, HpaII and BssHII, for example.

Briefly, detection of methylation of 5'CpG p16 DNA is accomplished by isolating DNA from the sample tissue followed by amplification, if desired, as described in the EXAMPLES herein. The DNA is thereafter subjected to restriction endonuclease analysis, either using methylation sensitive enzyme(s) alone, or in combination with other restriction endonucleases (e.g., EcoRI, HindIII) to produce a restriction map. Methylation at a site on the DNA that is usually recognized and cleaved by the methylation sensitive enzyme will prevent the enzyme from cleaving the DNA at that site. Consequently, a unique pattern of DNA fragments will be observed by gel electrophoresis and Southern blot analysis, for example, depending on the presence, or extent of methylation of the DNA.

The invention also provides a method of treating a cell proliferative disorder associated with altered p16 comprising administering to a subject with the disorder, a therapeutically effective amount of reagent which modulates p16 expression. The term "modulate" envisions the suppression of expression of p16 when it is over-expressed, or augmentation of p16 expression when it is under-expressed or when the p16 expressed is a mutant form of the polypeptide. As described above for 5'ALT associated disorders, several therapeutic regimes may be utilized to treat p16 associated disorders. For example, a pharmacological reagent such as a demethylating agent (e.g., 5-deoxyazacytadine) may be administered to the subject, for example locally at the site of the disorder, e.g., a tumor. In addition, a targeted gene delivery approach as described herein may also be utilized to treat a disorder associated with p16 expression.

SUMMARY

The identification of a novel member of the cell cyclin regulatory genes provides a useful tool for diagnosis, prognosis and therapeutic strategies associated with p16 and p15 mediated cell proliferative disorders. Measurement of polypeptide levels using antibodies is a useful diagnostic for following the progression or recovery from cellular proliferative diseases including cancer.

As discussed in the background section above, the gene encoding the tumor suppressor p16 and regions on chromosome 9p21 have been found to be deleted in certain cancers, thus allowing unchecked cellular proliferation to occur. Logically, if a gene encoding a tumor suppressor or a regulator of a tumor suppressor contains a polymorphism that compromises the activity of the suppressor then tumors may develop over time even without deletion of the gene encoding the suppressor. In the particular case of the 5'ALT gene, its presence on chromosome 9p21 suggests that both deletions and polymorphisms of the gene may contribute to the onset of certain familial and environmental cancers. Therefore, the invention also provides a method of detecting the presence or absence of all or particular regions of human chromosome 9p21, comprising contacting a sample containing human chromosomal DNA with a polynucleotide of SEQ ID NO:1, and detecting the hybridization of the chromosomal DNA with the polynucleotide of SEQ ID NO:1.

More specifically, the role of 5'ALT in forming alternate transcripts and truncated p16 and p15 polypeptides indicates that an excessive level of kinases can be expected to develop within cells that harbor 5'ALT gene deletions or polymorphisms that compromise the ability of p16 to inhibit CDK4, for example. Thus, while deletions of the 5'ALT gene may be indicative of a pre-malignancy or malignancy, polymorphisms in the gene (particularly polymorphisms in germline cells of persons with a familial history of 9p21-linked cancers) may be indicative of a susceptibility to develop a "cancer condition" (i.e., a condition which is causatively related to excessive cellular levels of CDK4).

In its broadest sense, the present invention allows the detection of any polymorphism in, or deletion of a p15, p16, or 5'ALT target nucleic acid sequence of diagnostic or therapeutic relevance, where the target nucleic acid sequence is present in a biological cell sample such as that heretofore subjected to histopathologic examination using techniques of light microscopy, such as the margins of a primary tumor or a regional lymph node. Thus, the target nucleotide sequence may be, for example, a mutant nucleotide, a restriction fragment length polymorphism (RFLP), a nucleotide deletion, a nucleotide substitution, or any other mammalian nucleic acid sequence of interest in such tissue specimens. As used herein the term "polymorphism" as applied to a target a p15, p16, or 5'ALT nucleotide sequence shall be understood to encompass a mutation, a restriction fragment length polymorphism, a nucleic acid deletion, or a nucleic acid substitution.

In the case of deletions and polymorphisms, this information can be used to diagnose a pre-cancerous condition or existing cancer condition. Further, by quantitating the number of cells in successive cell samples which bear and acquire methylation, a deletion, or a polymorphism at separate locations in the body and/or over time, the progression of a cancer condition can be monitored. Similarly, where methylation, a deletion, or a polymorphism is found in a patient who has not yet developed symptoms of a cancer condition (particularly one who carries the abnormality in germline cells and/or has a family history of a particular cancer condition), the deletion or polymorphism will be indicative of a genetic susceptibility to develop the cancer condition. Such susceptibility can further be evaluated on a qualitative basis based on information concerning the prevalence, if any, of the cancer condition in the patient's family history and the presence of other risk factors, such as exposure to environmental factors and whether the patient also carries cells having a deletion of the gene for cell cyclin inhibitors or regulators.

In order to detect the alteration of the wild-type 5'ALT gene in a tissue sample, means known in the art are used to enrich for tumor cells. Detection of point mutations may be accomplished by molecular cloning of the allele(s) present in the tumor tissue and sequencing the allele(s) using techniques known in the art. Alternatively, the polymerase chain reaction can be used to amplify gene sequences directly from genomic DNA preparations from the tissue (see EXAMPLES). Specific primers which can be used in order to amplify the gene will be discussed in detail in the EXAMPLES. Because 5'ALT resides in close proximity to the p15 and p16 loci on chromosome 9p21, 5'ALT specific primers can also be utilized for amplification and detection of polymorphisms, deletions, point mutations, etc., in the p15 or p16 gene, as well.

The following examples are intended to illustrate but not limit the invention. While they are typical of those that might be used, other procedures known to those skilled in the art may alternatively be used.

EXAMPLES

The finding that de novo methylation of a 5'CpG island led to transcriptional block of full length p16 in many neoplasms, led to the present finding of the presence of an alternative promoter or initiation site for p15 and p16. The present EXAMPLES show the identification of an abundant p16 and p15 alternative transcript generated from a novel 5'ALT sequence, involved in the complex regulation of these cell cycle related genes.

In addition, the following examples describe the transcriptional block of p16 by methylation of 5'CpG islands which is detected in many cancers cell lines and primary tumors examined herein.

Example 1

Materials and Methods
1. Cell lines and primary tumors

Cell lines used in this study included those derived from primary head and neck squamous cell carcinomas at Hopkins (003, 006, 011, 012, 020, 022, 029, 030) or elsewhere (A439, A549, UMSCC), Hela, and a normal lymphoblastoid line L89. Primary tumors included 14 non-small cell lung cancers, 8 small cell lung cancers, 15 pancreatic adenocarcinomas and 13 head and neck squamous cell carcinoma collected at the Johns Hopkins Hospital (diagnosis was confirmed by pathology). Tumors were microdissected to remove non-neopstic cells and genomic DNA or total RNA were extracted as described previously (Mao, L., et al., *Cancer Res.*, 54:1634–1637, 1994; Chomczynski, P. and Sacchi, N., *Analyt. Biochem.*, 162:156–159, 1997).

The following cell lines were obtained from A. F. Gazadar as a gift: NSCLC: A549, H125, H157, U1752, H460, H1155, H1299, H2106, H358, H720, H727; SCLC: H60, H64, H69, H82, H146, H209, H249, H1618. The two SCLC lines OH1 and OH3 were generated in our laboratory. RNA was kindly provided by M. Mabry and M. Borges. Primary lung, HNSCC, and brain tumors (malignant gliomas) obtained from surgical resection were processed as described previously (Vogelstein, et al., *N. Engl. J. Med.* 319:525–532, 1988). Only tumors with greater than 70% neoplastic tissue were used to isolate DNA for further analysis.

2. "Inverse" PCR

A specific antisense primer from the 3' untranslated region of p16 (5'- TCCCGAGGTTTCTCAGAG-3) (SEQ ID NO:2) was used for reverse transcription of total RNA (5 ug each from tumor or normal lymphoblastoid cell lines) by using 200 U Superscript II RNase HRT in the presence of dNTPs and double stranded cDNA was then synthesized following the manufacturer's protocol (GibcoBRL, Gaithersburg, U.S.A.). Self-ligation of the blunt end cDNAs was performed in 100 ul reaction volume containing 50 U T4 DNA ligase (GibcoBRL) as previously described (Zeiner, M. And Gehrig, U., *Biotechniques*, 17:1051–1053, 1994) 5ul of each ligation product was used for PCR amplification as described (Sidransky, et al., *Science*, 252:706–709, 1991) by utilizing primers in exon 2 of p16; the sense 5'-CAUCAUCAUCAUGATGTCGCACGGTACCTG-3' (SEQ ID NO:3) and antisense 5'-CUACUACUACUAACGGGTCGGGTGAGAGTG-3' (SEQ ID NO:4) primers were oriented away from each other. The PCR products were then cloned into a plasmid vector (pBSK, Strategene). At least 10 clones were sequenced for each sample by direct sequencing following the manufacture's protocol (Perkin Elmer) (see below).

3. RT-PCR

Total RNA was extracted from cell lines by the guanidium-isothiocyanate-phenol-chloroform method (Chomczynski, P. & Sacchi N., *Analyt. Biochem*, 162:156–159, 1987). Total RNA (5 mg) or poly-A (0.5 mg) was reverse transcribed by using Superscript II RNaseH (Gibco-BRL) reverse transcriptase (200 units) in the presence of hexamers (Pharmacia) and dNTP (Gibco-BRL). The cDNA was then amplified by PCR using the forward primer for exon 1 and the reverse primer for exons 2 or 3 (Kamb, et al., *Science* 264:436–440, 1994; and Serrano, et al., *Nature*,366:704–707, 1993) of p16 yielding a 428 or 477 kb fragment respectively, which was run on 1.5% agarose gel. As a control the 321 kb fragment of p53 was amplified simultaneously. All reactions were repeated at least once. p16 primer sequence were as follows: p16 exon1-sense: 5' TGGAGCCTTCGGCTGAC 3' (SEQ ID NO:15), p16 exon2-sense: 5' TCATGATGATGGGCAGCG 3' (SEQ ID NO:16), p16 exon2-antisense: 5' GGGACCTTCCGCGGCAT 3' (SEQ ID NO:17), P16 EAS: 5' TCCCGAGGTTTCTCAGAG 3' (SEQ ID NO:18). Primer sequence for p53 fragment (partial exon 3 and 4); sense: 5' TCCCAGAATGCCAGAGGC 3' (SEQ ID NO:19), antisense: 5' AGTACACGACACTGACGAAC 3' (SEQ ID NO:20).

2 $\mu$g total RNA was subjected to reverse transcription with random hexamers, dNTPs, and 200 U Superscript II RNase H RT (GibcoBRL) in a 20 $\mu$l reaction volume as above. PCR amplification was performed by using primers P1 (5'-AGTGGCGCTGCTCACCTC-3') (SEQ ID NO:5) and P2 (5'-TCCCGAGGTTTCTCAGAG-3') (SEQ ID NO:6) for the p16ALT cDNA fragment, and P1 and P3 (5'-GGGTGGGAAATTGGGTAAG-3') (SEQ ID NO:7) for the p15ALT cDNA fragment. The products were run on 1% agarose gel and visualized by ethidium bromide staining.

In the methylation studies, the cDNA was then amplified by PCR using the forward primer for exon 1 and the reverse primer for exons 2 or 3 of CDKN2/p16 yielding a 428 or 477 kb fragment respectively, which was run on 1.5% agarose gel. As a control, the 321 kb fragment of p53 (or β-actin) was amplified simultaneously. All reactions were repeated at least once.

4. RNAase protection assay 485 bp of a p16 cDNA fragment (including exon 1, 2, 3 and partial 3' UTR) was cloned into the pBSK vector (Strategene). An antisense p16 RNA probe containing γ-[$^{32}$P-UTP] was then synthesized by using a in vitro transcription kit and isolated by gel electrophoresis (Ambion). 100 ug of total RNA from each sample was co-precipitated with labelled probe and hybridized overnight at 45° C. After NRase treatment of hybridized products, samples were concentrated by ethanol precipitation, separated on 5% acrylamide/8M urea gel, and exposed to film.

5. Primer extension assay

An antisense primer of 5'ALT (5'-GGGTCACCAAGAACCTGC-3' (SEQ ID NO:8) was end labelled with 65 -[$^{32}$P-ATP] and T4 DNA polynucleotide Kinase (New England). 100 $\mu$g total RNA was used for each reaction. After co-precipitation of the primer and RNA, samples were incubated in the hybridization buffer at 30° C. for overnight. Reverse transcription was performed at 42° C. for 60 minutes with 200 U of Superscript II RNase H RT in the presence of dNTPs (GibcoBRL). After treatment with RNase H, samples were concentrated by ethanol precipitation and separated on 6% acrylamide/8M urea gel. A standard sequence of the p53 gene was used as a size marker after exposing to film.

6. Restriction mapping

Exon 1 of p16 was labeled by random priming and used to probe the chromosome 9 cosmid library LL-9 (constructed at the Biomedical Sciences Division, Lawrence Livermore National Laboratory, California 94550, sponsored by the U.S. Department of Energy.) The cosmids (217C4, 191G6,190G8, 190D10 and 9C1) were cut with restriction enzymes EcoRI, PstI, and HinfI, run on a 0.8% agarose gel and transferred to nylon membrane. Exons 1 and 2 of both p16 and p15 and 5'ALT were labelled by random priming and hybridized to the blots.

7. Sequence analysis

Primary tumor or cell line DNA was amplified by PCR with primers 5'-TCCCAGTCTGCAGTTAAGG-3' (SEQ ID NO:9) and 5'GTCTAAGTCGTTGTAACCCG-3' (SEQ ID NO:10) as described (Sidransky, 1991, supra). 10–50 ng of amplified DNA was utilized for each sequence reaction. Sequencing primers 5'-AGTGCATCAGCACGAGGG-3' (SEQ ID NO:11) and 5'-AACATGGTGCGCAGTTC-3' (SEQ ID NO:12) were labelled by γ-$^{32}$P-[ATP] at the 5' end and subjected to PCR amplification for 25 cycles using the AmpliCycle™ sequencing kit (Perkin Elmer) according to manufacturer's protocol. 2.5 $\mu$l of each amplified product was run on 6% acrylamide/8M urea gel and exposed to film.

p16 was amplified in two segments as described in Kamb, et al., (*Science* 264:436–440, 1994). UDP ends were added to each primer for rapid cloning into a CloneAmp vector (Gibco-BRL, Gaithersburg, Md.). Cloned products were used to transform competent DH5-a E. coli, and pooled clones were sequenced as described in van der Riet, et al, (Cancer Res., 54:25–27, 1994), using the amplification primers for sequencing.

The PE1 probe described in FIG. 3b was labeled by random priming and used to probe the chromosome 9 specific genomic library LL09NC01 constructed at the Biomedical Sciences Div., Lawrence Livermore National Laboratory, California 94550, sponsored by the U.S. Department of Energy. An additional 139 bp upstream of the published 5' UTR of p16 (HGD U12818) was derived from direct sequence analysis of glass-purified DNA from cosmid 191G6, using the Ampli-Cycle sequencing kit (Perkin-Elmer), under conditions described by the manufacturer with the antisense primer 5' CGCCGAGCGCACGCGGTC-CGCCCC 3' (SEQ ID NO:13).

8. TNT Assay

2 μg of total RNA was used for reverse transcription as described above in the presence of hexamers and dNTPs. PCR amplification was performed as described previously using primers TNT-P16 (Jen, et al., Cancer Res., 54:6353–6358, 1994) and P2 for p16 cDNA; P4 (5'-GGATCCTAATACGACTCACTATAGG-GAGACCACCATGGCGCTGCTCA CCTCTGGTG-3') (SEQ ID NO:14) and P2 for p16ALT cDNA in 25 μl reaction volume. After phenol-chloroform extraction and ethanol precipitation, ⅒ of the products from each sample was subjected to a TNT in vitro transcription and translation assay reaction in 10 μl volmne by using a commercial TNT kit (Promega). 2 μl of in vitro translated product was run on a 15% SDS-PAGE gel enhanced with Amplify® (Amersham) and exposed to film.

9. Immunoprecipitation

2 μl of in vitro translated product was incubated with either N-terminal or C-terminal polyclonal antibodies to p16 (Santa Cruz Biotechnology) in RIPA (10 mM Tris, pH7.5, 1% Na deoxycholate, 1% NP40, 150 mm NaCl and 0.1% SDS) at 4° C. overnight and then shaken with Sepharose A beads for 60 minutes. After washing three times with RIPA buffer, the products were run on 15% SDS-PAGE gels and exposed to films.

10. Analysis of allelic loss on chromosome 9p21

DNA from lung (NSCLC and SCLC), head and neck (squamous cell carcinoma) and brain (malignant gliomas) tumor specimens, cell lines, and non-neoplastic control tissue was analyzed for heterozygosity by amplification of dinucleotide repeat-containing sequences using PCR and the conditions previously described (Merlo, et al., Cancer Res. 54:640–642, 1994). The primers D9S156, D9S162, IFNa, D9S171, D9S126, D9S176, GSN, D13S133, D13S115, and D13S170 were obtained from Research Genetics (Huntsville, Ala.). After PCR amplification with annealing temperatures ranging from 54° to 61° C., products were separated by electrophoresis in denaturing 8M urea—6% polyacrylamide—formamide gels followed by autoradiography. In primary tumors, LOH was scored as described (Merlo, et al., supra). In cell lines, the absence of the second allele in all five highly polymorphic markers on 9 p was used as statistical evidence for LOH (Latif, et al., Cancer Res. 52:1451–1456, 1992).

11. Southern Hybridization

Southern blots were performed as described (de Bustros, et al., Proc. Natl. Acad. Sci. U.S.A., 85:5693–5697, 1988). Briefly, 5 mg of genomic DNA were digested with of EcoRI (10 U/mg) alone or in combination with the methylation-sensitive enzymes SmaI, EagI or SacII (15 U/mg each) for 16 h as specified by the manufacturers (Gibco-BRL and New England Biolabs), run on a 1% agarose gel, transferred to a Zeta-Probe GT nylon membrane (Bio-Rad), and probed with 25 ng of the 0.35 kb and 0.5 kb PCR products of exons 1 and 2 of p16 after random primer labelling (Feinberg, A. P. Vogelstein, B. A, Annal. Biochem. 137:266–267, 1984). The primer sequences for the PE1 probe are as follows: sense 5' GAAGAAAGAGGAGGGGCTG (SEQ ID NO:20), and antisense 5' GCGCTACCTGATTCCAATTC (SEQ ID NO:21), amplified with an annealing temperature of 60° C. by adding 3.6% formamide to the PCR buffer. The c-abl probe was provided by J.-P. Issa. The blots were then exposed in a phosphorimager (MolecularDynamics). All cases with a partial methylation pattern were repeated to exclude incomplete enzymatic activity.

12. Cell Culture

Cells were grown in RPMI 1640 with 5–10% fetal calf serum depending on the growth requirements of each line. To assess re-expression, 5-deoxyazacytidine was supplemented to the medium at concentrations of 0.3, 0.5 and 1 mmol, and cells were harvested after three and five days.

13. LOH

DNA from the 13 colon cancer cell lines was analyzed for heterozygosity by amplification of dinucleotide repeat containing sequences using PCR and conditions previously described (Merlo, et al., Cancer Res, 54:640–642, 1994.). The primers D9S156, IFNA, D9S171, D9S126 and D9S200, obtained from Research Genetics (Huntsville, Ala.) were used. The absence of the second allele in all five highly polymorphic markers on 9p was used as statistical evidence for LOH (Latif, et al., Cancer Res., 52:1451–1456, 1992.).

Example 2

Identification of 5'ALT

To identify the transcriptional start site of p16, a specific antisense primer (from the 3' untranslated region) was used for reverse transcription of total RNA from a normal lymphoblastoid cell line. Following reverse transcription, double stranded cDNA synthesis ligation was performed in large volume (Zeiner, 1994, supra). The resulting circular product was amplified by PCR (so called "inverse" or "bubble" PCR) utilizing primers in exon 2 of p16 oriented away from each other and then cloned into a plasmid vector. Ten individual clones were then sequenced completely. Although clones with the previously described exon 1 of p16 were identified, most clones (6 of 10) contained a novel 5' sequence spliced precisely onto (the first base of) exon 2 of p16. This novel 268 bp fragment (named 5'ALT for alternative) contained a theoretical open reading frame (ORF) but was not in frame with the putative coding sequence of exons 2 and 3 of p16 (FIG. 1a). Thus, the originally described exon 1 of p16 was completely excluded from this alternative transcript.

Figure 2A:
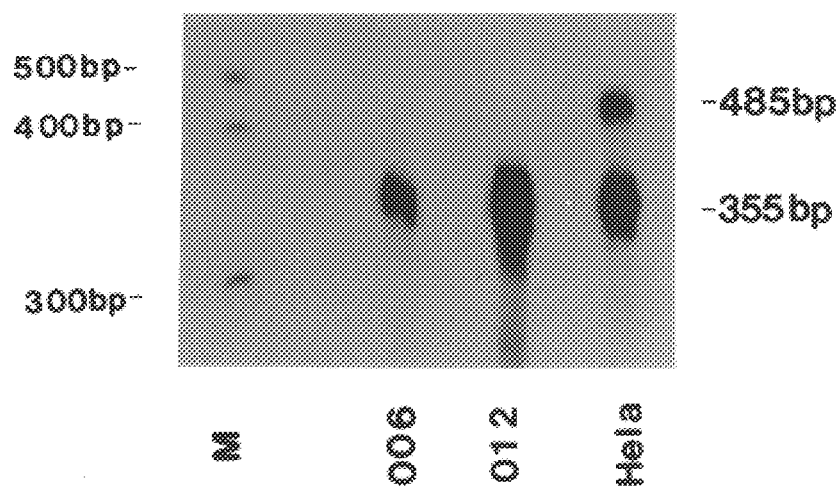
FIG. 2a shows an RNase protection assay used with a 485 bp p16$^{INK4A}$ cDNA fragment (icluding exon 1, 2, 3 and partial 3'UTR) as the probe. 006 and 012 designate head and neck squemous cell carcinoma cell lines in which methylation of the 5'CpG island of p16$^{INK4A}$ is associated with absence of full length p16$^{INK4A}$ mRNA (485 bp). Hela cell line contains normal p16$^{INK4A}$ mRNA and all cell lines contain a more abundant 355 bp smaller fragment.
Figure 2B:
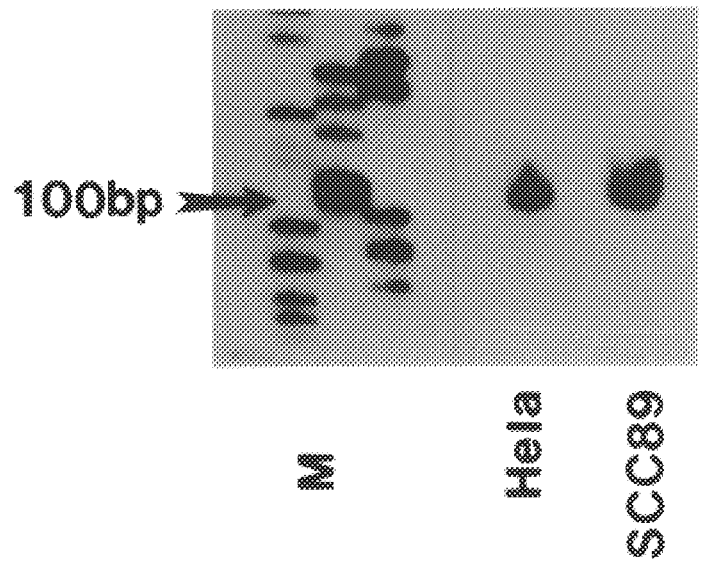
FIG. 2b shows a primer extension assay showing the expected initiation site of transcription for 5'ALT (100 bp from the primer) in both a Hela cell line and normal lymphoblastoid cell line (L89).

RNAase protection with a full length p16 probe demonstrated the presence of the originally described fill length p16 product (FIG. 2a). However, the smaller and more abundant product results from cleavage of the 5'ALT sequence with protection of the shared p16 portion that contains exons 2 and 3. This predominant tanscription initiation site was also confirmed by direct primer extension of total RNA (FIG. 2b).

Example 3

Genomic Localization Of 5'ALT

Genomic localization of the 5'ALT sequence was performed by using a specific oligomer derived from 5'ALT to probe a chromosome 9 cosmid library. One of the hybridizing cosmid clones contained both p16 and p15. EcoRI restriction mapping of this cosmid and other hybridizing clones yielded a small contig (approx 80 kb) of the region. Successive Southern blot hybridization with all exons of p16 and p15 (and the 5'ALT ORF) to the cosmid contig was performed. 5'ALT was found to be on the same 8.5 kb fragment with exon 2 of p15 and two cosmids contained 5'ALT but not exon 1 from p 15. These findings and those below are compatible with localization of 5'ALT upstream to exon 2 of p15 (FIG. 1b).

One of the cosmids was then used to derive the complete surrounding genomic sequence of 5'ALT (FIG. 1a) which is notable in several respects. First, the region is CpG rich and there is a GT rich region upstream of 5'ALT suggestive of a GT box promoter element. Second, a consensus Kozak element is contained at an AUG site at position 75 (nucleotide). Additionally, a long microsatellite ($CA_n$) repeat sequence is located downstream and has been confirmed to be highly polymorphic.

The localization of 5'ALT upstream to exon 2 of p15 (and extensive conservation of the 5' intron/exon boundary of exon 2 in both p16 and p15) led to the investigation of the presence of a 5'ALT p15 product. As for 5'ALT-p15, "inverse" PCR was performed with a p15 specific primer and a similar 5'ALT product was obtained which was spliced to exon 2 of p15. RT PCR of total RNA from eight tumor cell lines (without homozygous deletion of this region) confirmed the presence of both alternative transcripts (p15ALT and p16ALT) in all cases. Sequence analysis of 5'ALT sequences in these eight tumor cell lines and in several primary tumors with hemizygous loss of 9p21 has not yet revealed a point mutation.

Example 4

Transcription And Translation From 5'ALT

Figure 2C:
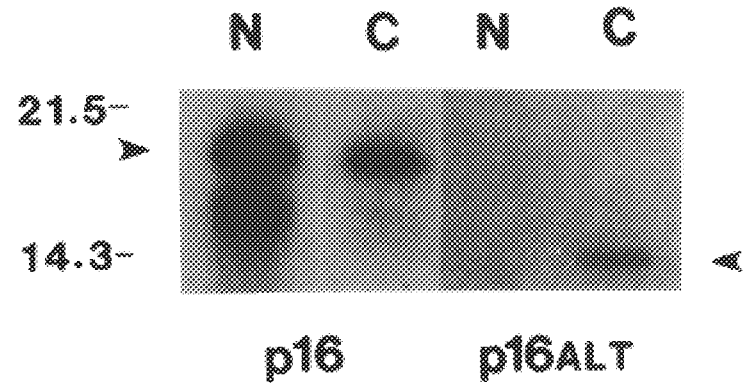
FIG. 2c shows immunoprecipitation of in vitro translated p16 and 5'ALT-p16 with a C-terminal antibody to p16(C), or an antibody to only the N-terminal portion of p16 (N). p16-5'ALT is recognized by the C-terminal antibody but not by the N-terminal antibody, whereas p16 is recognized by both antibodies.

Complete p16 and p16-5'ALT cDNA was amplified by RT-PCR and subjected to labelled in vitro transcripton and translation (TNT). As shown in FIG. 2c, the smaller p16-5'ALT product migrated at approximately 9–10 kD on SDS/PAGE gels. To see if his product was translated in frame from the third Met of p16 (just inside exon 2 and consensus Kozak sequence), immunoprecipitation was performed using polyclonal anti-p16 antibodies that recognize either the C-terminus or the N-terminus. As expected, the TNT p16ALT product was recognize by the C-terminal but not the N-terminal antibody providing strong evidence that this product lacked the N-terminal exon 1 coding sequence.

Example 5

The 5' End of p16 Contains CpG Island

The previously designated genomic sequence of the first exon of p16 and its untranslated surrounding areas (bases 1–340, Genome data base, U12818) and an additional 139 bases upstream of the first nucleotide derived from a genomic cosmid clone were used to check for the presence of a 5' CpG island. This stretch of DNA has a GC content of 67% and a CG:GC ratio of 0.77 defining a CpG island (FIG. 3). Open boxes denote the three coding exons, the shaded box stands for the 3'UTR of p16. Exon 1 resides in a 4.3 kb EcoRI restriction fragment, and is embedded in a CpG island. Methylation-sensitive, rare base cutting restriction enzymes include three SmaI (Sm), two SacII (Sa), and two EagI (E) sites. The density of CG and GC dinucleotides in the 479 bp sequence (including exon 1 of p16) is shown below the restriction map by vertical bars. PE1 denotes the location of the PCR generated probe, used for Southern analysis (FIG. 3b). Below are the expected fragment sizes recoded by his probe (not showing the sizes of fragments not recognized by this probe) when digested with the restriction enzymes shown, in the normally unmethylated status. * denotes the fragments produced by methylation of the 3' EagI site seen in normal tissues.

Figure 3A:
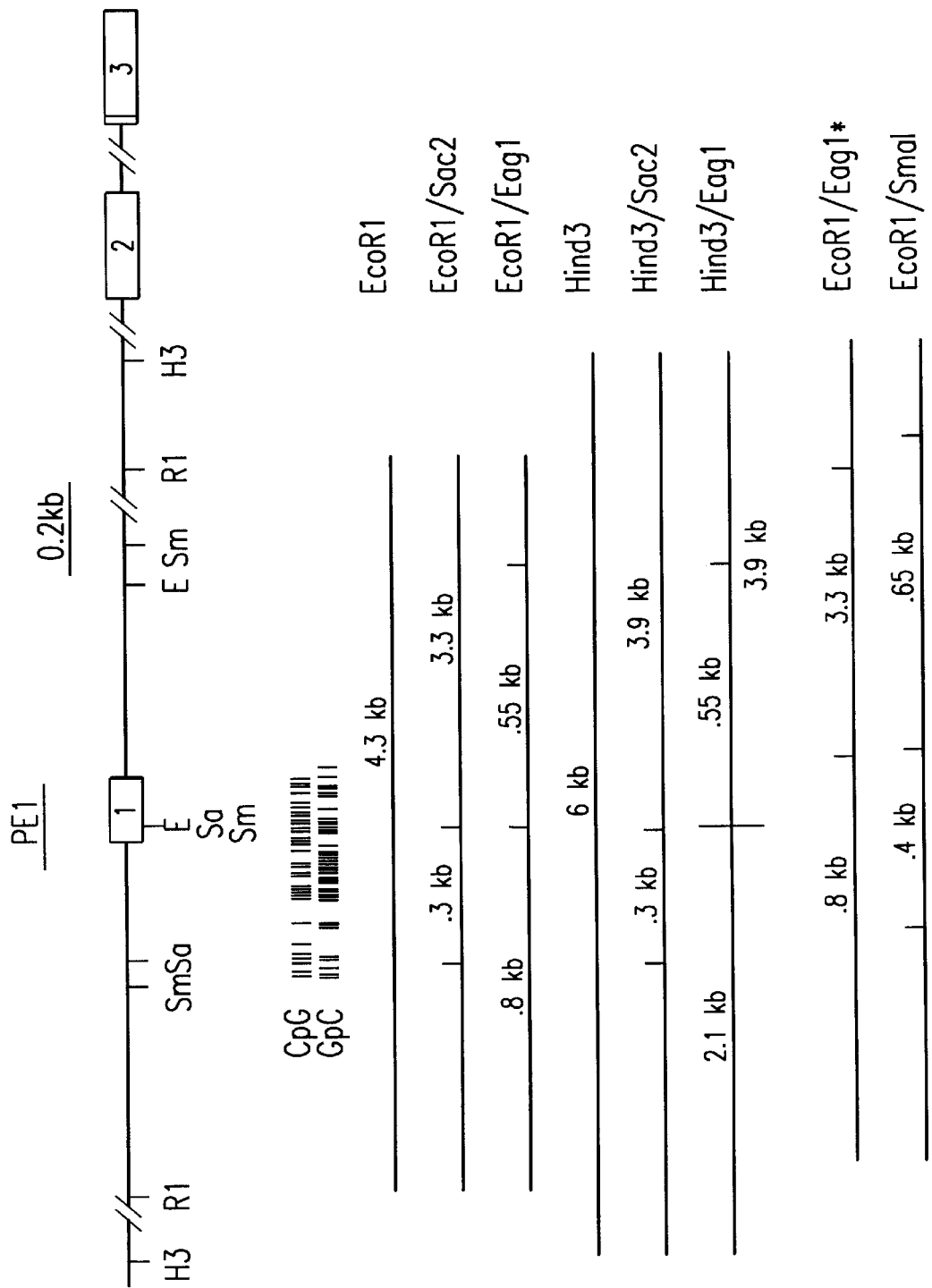
FIG. 3a shows the restriction map and CG dinucleotide density of p16.

The CpG density of 8.6% exceeds the theoretically expected frequency of CpG dinucleotides that equals $1/(4)^2$ or 6.2%. However, the actual frequency of CpG sites in mammalian DNA is only 1–2% due to transitions from 5-methyl cytosine to thymidine during the evolution of the vertebrates genome (Bird, A. P., Nature, 321:209–213, 1986; and Bird, A., Cell 70:5–8, 1992). A restriction map of the 4.3 kb genomic fragment of p16 reveals several rare cutting methylation-sensitive sites (FIG. 3a). In addition, this 479 bp sequence includes 4 HhaI, 3 ThaI and 2 HpaII sites. Double restriction digestion with the "flanking" cut (EcoRI) and methylation sensitive restriction enzymes (i.e. EagI, SmaI, or SacII yields a 4.3 kb fragment on Southern analysis if the restriction sites of a particular methylation sensitive enzyme are protected from cleavage due to methylation of the CpG dinucleotide. If the site is not protected, double restriction digestion with EcoRI and EagI, e.g., yields three fragments of 0.8, and 0.55 kb size, or 0.8 and 3.3 kb if the 3' restriction site is methylated. Likewise, double digestion with EcoRI and two other methylation-sensitive enzymes (SmaI or SacII) again yields a 4.3 kb "flanking" fragment, if the SmaI or SacII sites are methylated, and smaller fragments (0.65 and 0.35, or 3.3 and 0.3 kb, respectively), if they are not protected by CpG methylation (FIG. 3a).

Example 6

5' CpG Island Methylation Of p16 In Cancer Cell Lines

The 5' CpG island of p16 was analyzed for changes in DNA methylation. As expected, the SmaI and SacII sites were unmethylated in normal tissues of the lung, kidney, and blood lymphocytes (Bird, A., supra). Only the 3' EagI site, which lies outside of the CpG island, was partially methylated in some normal tissues. Nine non-small cell lung cancer (NSCLC), ten small cell lung cancer (SCLC), and ten head and neck squamous cell carcinoma (HNSCC) were analyzed. Cell lines with known homozygous deletions of p16 were excluded from this analysis (Nobori et al., Nature, 368:753–756, 1994). Seven of nine NSCLC cell lines were fully methylated; double-digestion with any of the three methylation-sensitive restriction enzymes in conjunction with EcoRI yielded the same 4.3 kb band seen with EcoRI digestion alone, indicating protection from restriction by methylation (FIG. 4). The two remaining NSCLC cell lines were not methylated at these sites. Three of the seven HNSCC cell lines which share common histological features with squamous cell carcinoma of the lung (part of NSCLC) were also found to be methylated at the 5' CpG island of p16, while the remaining four lines were unmethylated at this region (Table 1). In contrast, only one (H1618) of the ten SCLC cell lines showed CpG island methylation in this distinct area, while none of the restriction sites for the three methylation-sensitive enzymes were protected by CpG methylation in the remaining nine cell lines. It is noteworthy that methylation is not uniformly spread across this particular region on chromosome 9p21, since other CpG-rich regions of p16 and a neighbouring gene (p15/MTS2) did not reveal a concomitant pattern of methylation. Concordant patterns of de novo methylation were obtained using the methylation-sensitive enzymes HhaI and HpaII.

Figure 4A:
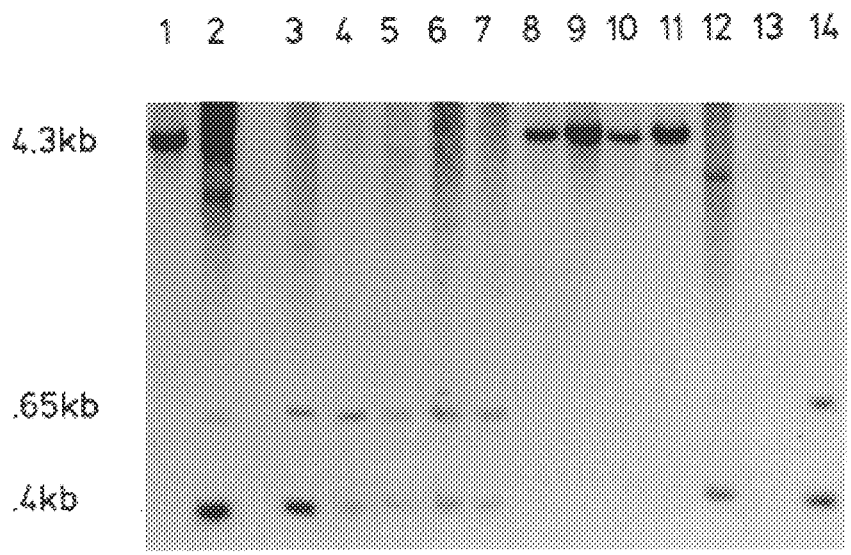
FIGS. 4a–c show methylation of the 5'CpG island of p16 in lung cancer cell lines.

FIG. 4a shows Southern blot analysis with the PE1 probe from p16 reveals the 4.3 kb "flanking" cut with EcoRI alone (lane 1). Digestion with SmaI alone yielded two smaller fragments (0.65 and 0.35 kb) in normal tissue (lane 2), indicating all sites are unmethylated. SCLC cell lines had the normal unmethylated pattern (lanes 3–7) while most NSCLC cell lines were methylated at all three SmaI sites, leading to protection of the "flanking" 4.3 kb band (lanes 8–10). Only one of ten SCLC lines was methylated (lane 11) and two NSCLC lines were unmethylated (lanes 12 and 14); lane 13 demonstrates a homozygous deletion of p16 in the lung cancer line H460.

Figure 4B:
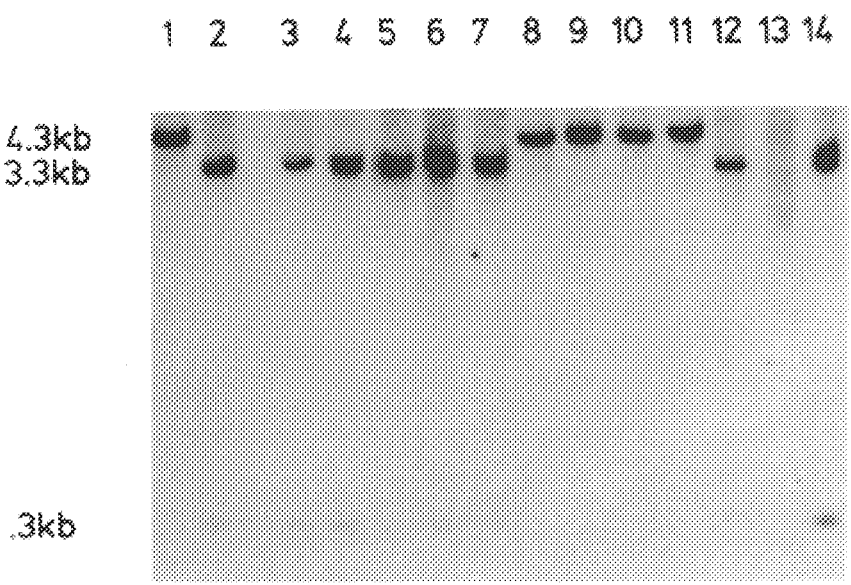

FIG. 4b shows the same cell lines as shown in FIG. 4a above had methylated (lanes 2–7, 12, 14) or unmethylated CpG sites (lanes 8–11) when restricted with SacII, yielding two restriction fragments (3.3 and 0.3 kb) or 4.3 kb, respectively.

Figure 4C:
Figure 7A:
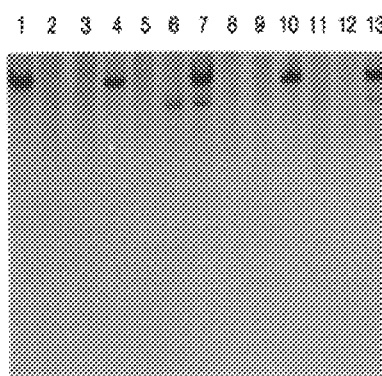
FIGS. 7a–d show Southern blots depicting methylation and homozygous deletion of p16 DNA in cancer cell lines.
Figure 7B:
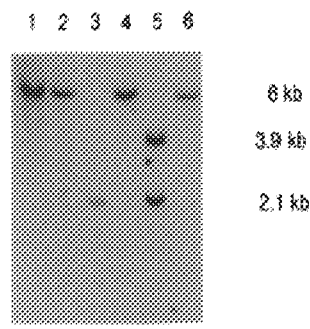
Figure 7C:
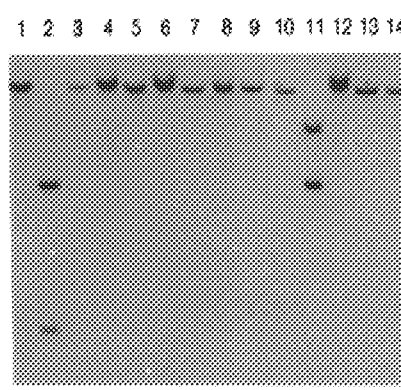
Figure 7D:
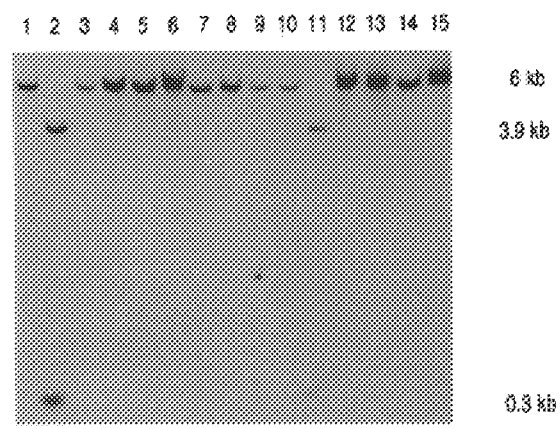

FIG. 4c shows reverse-transcription of p16 of these cell lines demonstrates lack of the 428 bp product in the methylated cell lines (lanes 8–11) and the homozygously deleted cell line (lane 13) whereas all the unmethylated cell lines express the gene. The p53 control RT-PCR product (321 bp, partially spanning exons 3 and 4) was a control for RNA integrity.

TABLE 1

5' CpG ISLAND METHYLATION RELATED TO ALLELIC STATUS AND SEQUENCE ANAYLSIS OF CDKN2/p16 IN CELL LINES AND PRIMARY TUMORS

| Histology | $n^a$ | LOH (9p21) | Methylated (mRNA expressing lines/total lines tested) | Unmethylated | p16-sequencing wt (mut) |
|---|---|---|---|---|---|
| Cell lines | | | | | |
| NSCLC | 9 | 6 | 7(0/6) | 2(2/2) | 9(0) |
| SCLC | 10 | 7 | 1(0/1) | 9(6/6) | 10(0) |
| HNSCC | 7 | 7 | 3(0/3) | 4(4/4) | 6(1) |
| Primary human cancers | | | | | |
| NSCLC | 27 | 21 | 7 | 20($ND^b$) | 20(0) |
| SCLC | 5 | 3 | 0 | 5(ND) | 4(0) |
| HNSCC | 4 | 3 | 1 | 3(ND) | 4(0) |
| Gliomas | 13 | 8 | 3 | 10(ND) | 13(0) |

$^a$Sample number after exclusion of homozygous deletions of p16
$^b$not done, NSCLC = non-small cell lung cancer, SCLC = small cell lung cancer, HNSCC = head and neck squamous cell carcinoma, gliomas = malignant astrocytomas.

Example 7

5'CpG Island Methylation, Allelic Loss And Sequence Analysis Of p16

Five microsatellite markers on chromosome 9p (D9S156, D9S162, IFNa, D9S126 and D9S171) in the cell lines studied above were tested to screen for loss of heterozygosity (LOH) of chromosome 9 (Latif et al., Cancer Res., 52:1451–1456, 1992). As expected, most of the cell lines displayed LOH of 9p, and importantly, LOH on chromosome 9p was associated with 5'CpG island methylation of p16. Moreover, five of seven methylated NSCLC cell lines had lost the wild-type allele, and the two cell lines which retained heterozygosity completely methylated both alleles of the 5'CpG island of p16. In contrast, seven of ten SCLC lines had LOH on chromosome 9p21, while only one of these lines methylated the 5'CpG island of p16.

Sequence analysis of exons 1 and 2 of p16 in cell lines disclosed only one mutation in a HNSCC cell line. This base pair change in the cell line FADU produced a mutation of the splice acceptor site of exon 2 (G-T, 150 nt), causing exclusion of exon 2. The FADU line contained an unmethylated 5'CpG island of p16, as would be expected since methylation and point mutation are considered as two independent modes of gene inactivation.

Interestingly, primers designed to amplify exons 2 and 3 of the p16 cDNA, yielded the appropriate size product of 352 bp in all cell lines regardless of 5'CpG island methylation status, but not in cells with homozygous deletions. Further analysis disclosed a novel cDNA product that consists of a distinct 5'UTR (5'ALT) spliced to exons 2 and 3 of p16 cDNA (p16 5'ALT). This product, excluding exon 1 of p16, initiates transcripion at a locus upstream 16.

Example 8

Cell Lines Methylated At The 5'CpG Island CDKN2/p16 Show Lack of Transcription

5'CpG island methylation is usually associated with loss of transcription. Therefore, RNA derived from 23 cell lines was subjected to reverse transcriptase (RT)-PCR using primers amplifying a 428 bp cDNA stretch corresponding to the first and second exon of p16. None of the methylated cell lines (6 NSCLC, 1 SCLC, 3 HNSCC) expressed p16, while a control RT-PCR product of exons 3 and 4 of p53 was readily detectable. In contrast all the unmethylated cell lines (2 NSCLC, 6 SCLC, 4 HNSCC) expressed this 428 bp product of p16. As for other genes on the X-chromosome or in imprinted regions, it is methylation at the 5'CpG island that consistently and reproducably correlated with the transcriptional block of p16.

Interestingly, primers designed to amplify exons 2 and 3 of the CDKN2/p16 cDNA, yielded the appropriate size product of 352 bp in all cell lines regardless of 5'CpG island methylation status. Further analysis disclosed a novel cDNA product that consists of a distinct 5'UTR spliced to exons 2 and 3 of CDKN2/p16 cDNA. This product, excluding exon 1 of CDKN2/p16, initiates transcription at a locus upstream of p16.

Example 9

Re-Expression Of p16 By 5-Deoxyazacytidine

In order to test the hypothesis that 5'CpG island methylation of p16 indeed blocks gene expression, five methylated cell lines (3 NSCLC and 2 HNSCC) were subjected for 3–5 days to different dosages (0.3–1mmol) of the demethylating agent 5-deoxyazacytidine.

FIG. 5a shows Southern blot analysis with the PE1 probe from p16 reveals the 4.3 kb "flanking" cut with EcoRI alone (lane 1). The addition of EagI yields the expected smaller fragments (3.3, 0.8 and 0.55 kb) in normal tissue which is unmethylated (lane 2). In HNSCC cell lines, Lane 3 shows a cell line with a homozygous deletion of p16, and lanes 4 and 6 show fully methylated cell lines; lanes 5 and 7 are unmethylated.

FIG. 5b shows the upper panel shows lack of p16 transcription in cell lines with homozygous deletion (lane 3) or methylation (lanes 4 and 6) of this gene. After 5-deoxyazacytidine treatment, the methylated cell lines re-express p16 (lower panel lanes 4 and 6). The unmethylated cell lines constitutively express this gene (lanes 5 and 7).

FIG. 5c shows two additional NSCLC cell lines demonstrate aberrant methylation (lanes 2 and 7) when restricted with with EcoRI and SmaI, compared to an unmethylated cell line (lane 1). After 5-deoxyazacytidine treatment with 1 and 0.5 mmol for 3 days (lanes 3 and 5) and 5 days (lanes 4 and 6), demethylation was seen in line H 1752 with all dosages and time points tested. Partial demethylation is also shown in line H157 after 5-deoxyazacytidine treatment (lane 8).

FIG. 5d shows the transcriptionally silenced lanes U1752 and H157 (lanes 2 and 7) re-express p16 after 5-deoxyazacytidine treatment at all doses and times, yielding a 428 bp product (lanes 3–6, 8). The 321 bp control product of p53 was always transcribed.

At each dose and time tested, all five cell lines re-expressed the message of p16 as assessed by RT-PCR (FIG. 5). Treatment with 5-deoxyazacytidine lead to partial demethylation of the monitored CpG sites (FIG. 5c) precisely associated with reversal of the transcriptional block of p16 (FIG. 5d). Azacytidine had profound effects on cell growth, morphology, and viability. However, these effects were non-specific and observed in cell lines with homozygous deletions of p16, and with retention of p16 alleles independent of methylation status. Therefore, we cannot attribute these non-specific effects to re-expression of p16, since other genes might also be affected by azacytidine.

Example 10 b 5'CpG Island Methylation Of p16 In Primary Human Neoplasms

Since deletions and point mutations of p16 were frequently found in cell lines, but appeared less often in primary tumors (Spruck, et al., *Nature*, 370:183–184, 1994; Zhang, et al., *Cancer Res.* 54:5050–5053, 1994; Xu, et al., *Cancer Res.*, 54:5262–5264, 1994; and Okamoto, et al., *Proc. Natl. Acad. Sci. U.S.A.* 91:11045–11049, 1994), de novo methylation of p16 is present in primary fresh tumor specimens was examined. Forty-nine primary neoplasms (27 NSCLC, 5 SCLC, 13 malignant gliomas, and 4 HNSCC) were subjected to Southern blotting, using the methylation-sensitive restriction enzymes SmaI, EagI, SacII, as outlined above. In an initial Southern blot screening of a larger number of tumors with the EcoRI "flanking" cut alone probed with the PE1 (FIG. 3b), and then compared to the single copy control probe c-abl on chromosome 9q34, homozygously deleted samples were excluded from further analysis (FIG. 6).

FIG. 6a shows one malignant glioma (G18) demonstrates homozygous deletion of p16 while another (G7) displays retention. Hybridization with the single copy c-abl probe (chromosome 9q34) serves as a loading control.

FIG. 6b shows four NSCLC (lanes 2, 4, 6, 9) display de novo methylation of p16 at the SacII site (after double restriction digestion with EcoRI and SacII) which is not methylated in adjacent normal lung tissue (lanes 1, 3, 5). NSCLC L16 does not exhibit de novo methylation. Two glioblastomas (lanes 10 and 11), and one HNSCC (lane 12) are also methylated.

FIG. 6c shows the same tumors described in 6b display concordant methylation patterns after EagI and EcoRI double restriction digest (lanes 1–6).

Seven of 25 NSCLC showed the same aberrant methylation of p16 as described in cell lines that showed complete transcriptional block, involving nearly all the CpG sites in the 5'CpG island that were monitored by the three methylation-sensitive restriction enzymes. In contrast, 21 control DNA samples derived from kidney, peripheral blood lymphocytes, and corresponding normal lung tissue did not display any detectable methylation at these restriction sites. Tumor samples usually compose a heterogeneous mixture of normal and neopstic cells. This can pose some difficulty to the precise assessment of the rate of homozygous deletions. However, protected CpG sites can easily be attributed to tumor DNA since corresponding normal tissue never was found to be methylated.

Example 11

Methylation And Homozygous Deletion Of p16 DNA In Cancer Cell Lines

Exon 1 of p16 lies in a typical CpG island, as described in the above Examples, which is unmethylated in all normal tissues tested. Restriction with a non-methylation sensitive restriction enzyme, such as HindIII or EcoRI, convenient flanking cut which when combined with a methylation sensitive enzyme (such as EagI, SacII, or SmaI) allows rapid determination of the methylation status of this CpG island. This approach was used to study breast and renal cancer, which have frequent homozygous deletion of p16 (Kamb, et al., *Science*, 264:436–440, 1994)

FIG. 7 shows Southern blots depicting methylation and homozygous deletion of p16 DNA in cancer cell lines. In each panel, the highest molecular weight band (4.3 kb for A and 6.0 kb for B–D) reflects fill methylation of the methylation sensitive site (EagI or SacII). (A) Breast cancer cell lines. Lane 1 is DNA restricted with EcoRI alone for reference, while DNA in lanes 2–7 is restricted with EcoRI and SacII, and in lanes 8–13 with EcoRI and EagI. Cell lines shown are Hs578t (lanes 2,8), MCF-7 (lanes 3,9), T47D (lanes 4,10), MDA-MB-231 (lanes 5,12), MDA-MB468 (lanes 6,11) and ZR-75-1 (lanes 7,13). (B) DNA from prostate cancer cell lines restricted with HindIII and EagI. HindIII restricted DNA (lane 1) for reference, DuPro (lane 2), DU145 (lane 3), PC3 (lane 4), LNCaP (lane 5), TSU-Pr1 (lane 6). (C) Colon cancer cell lines. Lanes 1 and 2 are DNA, for reference, for an unmethylated lung cancer cell line restricted with HindIII (lane 1) or HindIII and EagI (lane 2). Lanes 3–15 are all restricted with HindIII and EagI, and represent, in order Colo320, WIDR, SW48, HT29, SW837, SW1463, SW948, SW1116, SW1417, Colo205, RKO, CaCO2, SW480. (D) DNA from the same colon cancer cell lines, restricted with HindIII and SacII, and shown in identical order to (C).

Southern analysis confirmed homozygous deletions of p16 in human breast cancer cell lines MDA-MB231 and MCF-7 (Kamb, et al., *Science*, 264:436–440, 1994.) and Hs578t (Xu, et al., *Cancer Res.*, 54:5262–5264, 1994.), since hybridization with exon 1 (FIG. 7a) or exon 2 of p16 produced no visible bands, while control probes revealed adequate high molecular weight DNA. However, in two breast cancer cell lines (ZR75-1 and T47D) restriction with flanking enzymes and either of the methylation sensitive restriction enzymes EagI or SacII produced a pattern of complete (T47D) or predominant (ZR75-1) methylation (FIG. 7a), while one breast cancer cell line (MDA-MB468) was unmethylated. Renal carcinomas previously analyzed for mutations and hypermethylation of VHL were also examined (Herman, et al., *Proc Natl Acad Sci USA*, 91:9700–9704, 1994.). Of 26 cell lines examined, 13 had homozygous deletion, consistent with rates of homozygous deletion previously reported (Kamb, et al., supra). However, 6 of the remaining 13 cell lines displayed abnormally hypermethylation p16 (Table 2).

TABLE 2

INACTIVATION OF p16 IN CELL LINES AND PRIMARY TUMORS

|  | Homozy-gously deleted | Methylated p16 | Inactivated p16 | Intact[a] p16 |
| --- | --- | --- | --- | --- |
| Cell lines (n) | | | | |
| Breast Cancer (6) | 3 (50%) | 2 (33%) | 5 (83%) | 1 (17%) |
| Prostate Cancer (5) | 0 | 3 (60%) | 3 (60%) | 2 (40%) |
| Colon Cancer (13) | 0 | 12 (92%) | 12 (92%) | 1 (8%) |
| Renal Cancer (26) | 13 (50%) | 6 (23%) | 19 (73%) | 7 (27%) |
| Primary tumors (n) | | | | |
| Breast Cancer (16) | 0[b] | 5 (31%) | 5 (31%) | 11 (69%) |
| Colon Adenoma (6) | 0[b] | 1 (16%) | 1 (16%) | 5 (84%) |
| Colon Cancer (20) | 0[b] | 8 (40%) | 8 (40%) | 12 (60%) |

[a]Tumors were not sequenced to exclude point mutations, which have not been found or are rare in these tumor types.
[b]Failure to detect homozygous deletion may result from residual normal tissue.

Figure 8A:
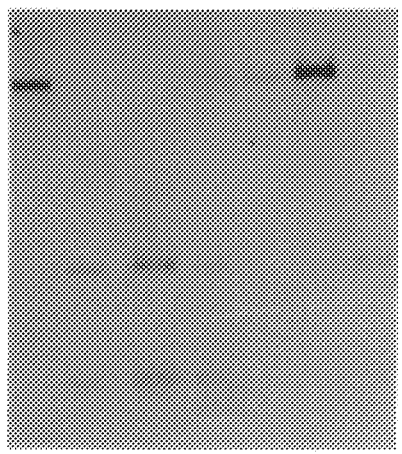
FIGS. 8a–c show Southern analysis of methylation of primary neoplasms.
Figure 8B:
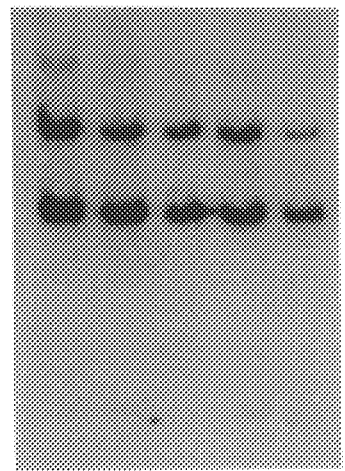

Primary tumors also displayed aberrant methylation of p16, with a line of renal cell carcinoma providing a vivid example. DNA from this renal cell carcinoma was hypermethylated at p16 in cell lines obtained from the primary and a metastatic tumor from the same patient. In addition, DNA from the original primary tumor and a metastasis from this patient, contained the same hypermethylated alleles of p16, (FIG. 8a). As in FIG. 7, the highest molecular weight fragment (3.6 kb in A or 6.0 kb in Band C) represent complete methylation of the methylation sensitive restriction sites (SmaI or SacII). (A) Renal cancer. DNA from normal kidney DNA restricted with XbaI (lane 1) or XbaI and SmaI (lane 2) are shown for reference. Lanes 3–7 show DNA from a single patient restricted with both XbaI and SmaI, including normal kidney (lane 3), primary renal carcinoma (lane 4) and the cell line derived from this primary (lane 5), metastatic tumor (lane 7) and the cell line derived from this metastatic tumor (lane 6). In primary tumors, normal unmethylated alleles present likely represent contaminating normal tissue. (B) Breast tumor DNA restricted with HindIII and EagI showing examples having hypermethylated alleles (lanes 1,2,4) and those without methylated alleles (lanes 3,5). (C) DNA from normal colonic mucosa (lanes 1, 3, 5) and colon cancer (all other lanes) are shown following restriction with HindIII and SacII. Some primary colon cancers had hypermethylated p16 alleles (lanes 2, 4, 6, 7, 8, 12) while others were unmethylated (lanes 9, 10, 11, 13).

These data indicate that the aberrant methylation was present in vivo and occurred prior to metastatic spread. DNA from this patient's normal adjacent kidney, along with four other adjacent normal kidneys and two kidneys from patients without cancer, did not contain these hypermethylated alleles. In primary breast cancer, 5 of 16 tumors (31%) also had hypermethylated p16 alleles. In the breast tumors, this p16 methylation was more difficult to detect, but confirmed on repeat analysis, even though these tumors contained a significant amount of normal tissue blunts the sensitivity of the analysis.

Figure 8C:
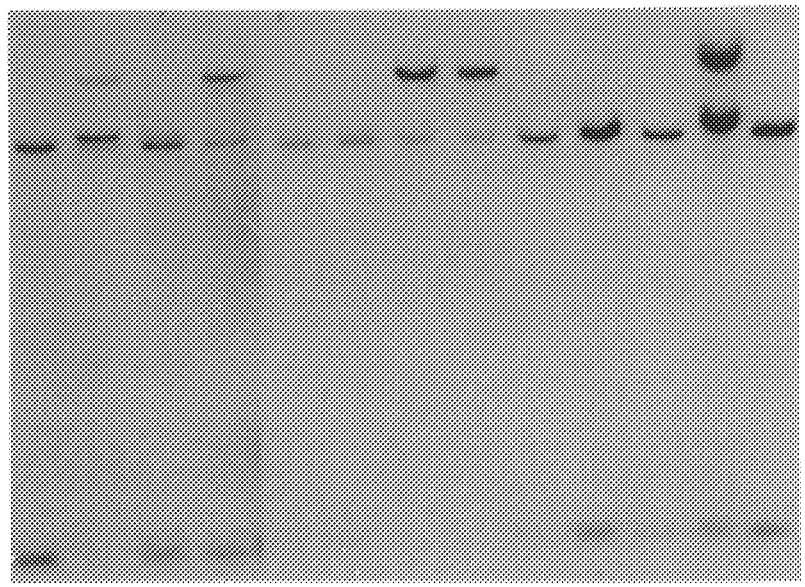

These findings confirmed that p16 methylation frequently occurs in common tumors in which homozygous deletions are also a common mechanism of inactivation. However, we have also found the methylation events in common cancers where homozygous deletions of p16 have never (colon) or rarely (prostate) been described (Kamb, et al, supra). In 3 of 5 prostate cancer cell lines (PC3, TSUPr1 and DuPro-1) and 12 of 13 colon cancer cell lines, the p16 CpG island of exon 1 was completely methylated, while only two prostate cancer cell lines (LNCaP and DU145) and one colon cancer cell line were unmethylated (SW1417) (FIG. 7). None of these 18 cell lines had homozygously deleted the gene, consistent with prior observations. In 20 primary colorectal carcinomas, we again found no evidence of homozygous deletion in this tumor type, but 8 of the 20 tumors (40%) had aberrant CpG island methylation in the 5'CpG island of p16 (FIG. 8c). In contrast, p16 was unmethylated in 22 normal adjacent colon mucosas and normal mucosas from individuals without cancer. Also examined were 6 adenomatous polyps, the preinvasive lesion from which colorectal carcinoma arises, for evidence of hypermethylation at p16. One large 40 mm adenoma had aberrant methylation of p16, while the remaining 5 smaller polyps displayed the normal methylation pattern, suggesting that inactivation of p16 by methylation occurs during progression from this early lesion to the carcinomatous lesion. These overall results in colon and prostate cancer were surprising and demonstrate that p16 is much more frequently inactivated in human tumors than previously realized.

These findings for hypermethylation of p16 in colon cancer were further striking, because not only homozygous deletions, but also LOH is not frequent for 9p21 in this tumor type. These cell lines were for evidence of LOH. Four of 13 colon cancer cell lines retained just 1 allele, while 7 cell lines, including the single colon cancer cell line (SW1417) with an unmethylated p16, had retained both alleles. Two other cell lines were considered non-informative, since they were heterozygous for only some of the 5 markers. Retention of both alleles in 6 of the cell lines with aberrant methylation of p16 suggests that both alleles are inactivated by hypermethylation without loss of the other allele.

Figure 9:
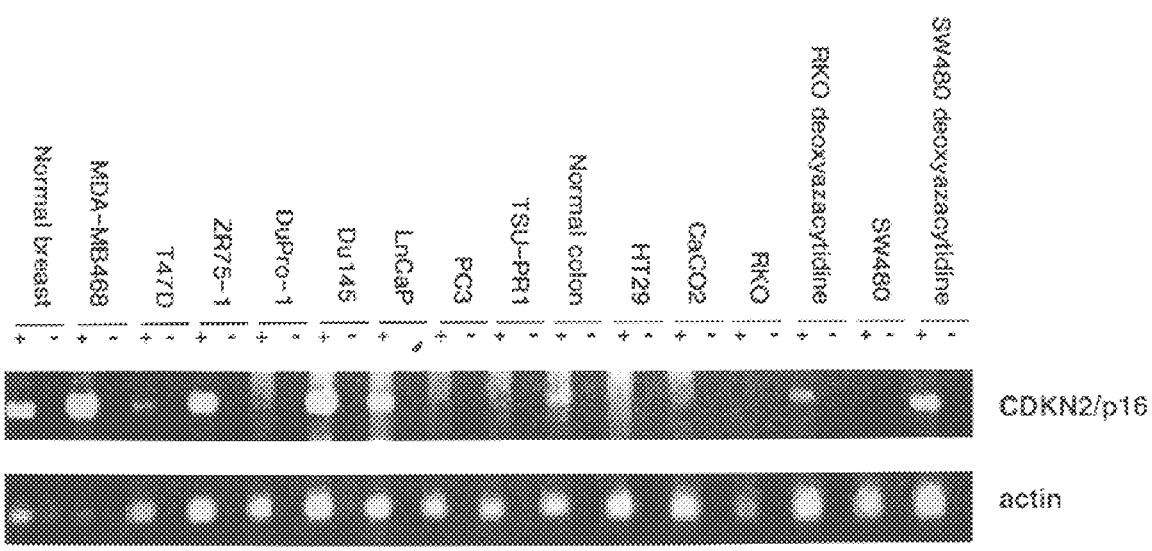
FIG. 9 shows RT-PCR analysis for expression of p16.

Hypermethylation in this 5' promoter region was associated with lack of transcription of the normal mRNA as shown in the previous Examples. Cell lanes of breast, prostate and colon cancer were therefore examined for expression by RT-PCR (FIG. 9). Cancer cell lines and corresponding normal tissue are shown. Analyses included samples with RT (+) and without RT (−). The expected 428 bp p16 product and 400 bp actin products are labelled at right. p16 gene mRNA was seen in the colon cancer cell lines RKO and SW480 only after treatment with 5-deoxyazacytidine.

SUMMARY

None of cell lines (T47D, DuPro-1, PC-3, TSU-PR1, HT29, CaCO2, SW480, RKO) fully methylated in this region of p16 expressed the expected product (minimal expression was seen in T47D). In contrast, normal breast and 3 of 4 tested colon mucosa samples had readily detectable p16 message. The unmethylated cell lines of breast and prostate cancer also expressed the gene (MDA-MB468, Du145, LNCaP). The breast cancer cell line ZR75-1, which was partially methylated, expressed p16 message. To confirm that this DNA methylation was essential for loss of transcription, the colon cancer cell lines RKO and SW480 was treated with the demethylating agent 5-deoxyazacytidine for 3 days. As in our studies of lung and head and neck tumors, both colon cancer cell lines had detectable p16 mRNA after treatment with 5-deoxyazacytidine, suggesting that the aberrant DNA methylation is essential for maintaining transcriptional silencing.

Aberrant methylation of p16 is analogous to homozygous deletion in terms of providing a selective growth advantage to tumor cells. The inverse relation of both aberrant methylation and homozygous deletion to genetic alterations of Rb lends further evidence to the concept that both genes act in the same pathway of cell cycle control, as previously reported (Okamoto, et al., *Proc Natl Acad Sci USA*, 91:11045–11049, 1994; Shapiro, et al., *Cancer Res*, 55:505–509, 1995). The present data amply validate this concept. The only breast cancer cell line with an intact CDKN2/p16 gene, MDA-MB468 has previously been reported to have mutant Rb, while the others have wild type Rb(MCF-7, MDA-MB-231, Hs578t, T47D) (T'Ang, et al., *Science*, 242:263–266, 1988). In fact, colon cancers have the most frequent inactivation of p16 by aberrant methylation, and have not been shown to inactivate Rb in studies which include many of the cell lines examined (Gope, R. and Gope, M. L. *Mol Cell Biochem*, 110:123–133, 1992). The impact of these cell cycle regulatory genes on proliferation rates is further reflected by the finding in prostate cancer cell lines, where the four lanes having inactivation of either p16 (DuPro-1, PC3, TSU-PR1) or Rb (DU 145) (Bookstein, et al., *Science*, 247:712–715, 1990), have a mean in vitro doubling time of 30 hours (range 22–hrs), (Stone, et al., *Int J Cancer*, 21:274–281, 1978; Gingrich, et al., *J Urology*, 246:915–919, 1991; Kaighn, et al., *Investigative Urolog*, 17:16–23, 1979; and Iizumi, et al. *J Urology*, 137:1304–1306, 1987) while the only cell line with both genes intact, LNCaP, has a cell doubling time of 60 hours (Horoszewicz, et al., *Cancer Res*, 43:1809–1818, 1983).

A consistent observation in the present EXAMPLES is that cell lines have a higher rate of abnormalities of p16 than do primary tumors (Cairns, et al., *Science*, 265:415–417, 1994; Okamoto, et al, *Proc Natl Acad Sci USA*, 91:11045–11049, 1994; Cheng, et al., *Cancer Res*, 54:5547–5551, 1994; Ohta, et al., *Cancer Res*, 54:5269–5272, 1994; Spruck et al., *Nature*, 370:183–184, 1994; Xu, et al., *Cancer Res*, 54:5262–5264, 1994; and Merlo, et al., supra). For homozygous deletions of the gene, this may in part represent the technical problems of detecting DNA loss in tumors contaminated by normal cells. Detection of aberrant DNA methylation of the p16 gene is not so limited by this problem, since gain of an abnormal band on Southern blots is more readily detectable even if it represents contribution from only a percentage of cells. In any case, the incidence of inactivation of p16, through either homozygous deletions of aberrant methylation, may be an underestimation in non-cultured samples of many tumor types.

Alternatively, abnormalities of p16 may be present in subpopulations of cells which are expanded during tumor progression and may be selected for in cell culture. Higher rates of mutation in cell lines than primary tumors have been reported for p53 and Rb in lung and breast cancer (T'Ang, et al., supra; and D'Amico, et al., *Oncogene*, 7:339–346, 1992). This finding may reflect selection of subclones of cells within an individual tumor which have a growth advantage that facilitates the establishment of an immortal cell line. However, the importance of p16 in vivo is still supported by the consistent alteration in the primary tumors of lung, glioma, colon and breast cancer. In brain tumors (Walker, et al., *Cancer Res*, 55:20–23, 1995) and lung carcinomas (Okamoto, et al., *Cancer Res*, 55:1448–1451, 1995), the later stage tumors have also been reported to have higher rates of homozygous deletion of p16 suggesting that p16 abnormalities may be late progression events for these tumors as well.

The presence of other AUG sites and a long UTR in 5'ALT favors diminished translation of the 5'ALT transcripts (Kozak, M., *Ann. Rev. Cell Biol.*, 8:197–225, 1992). The TNT studies presented herein much weaker translation efficacy for p16ALT in comparison to p16 (FIG. 2c). Other Cylcin/CDK inhibitors are known to undergo extensive transcriptional regulation and in the case of p27$^{Kip1}$, unusual post-transcriptional regulation (Hunter, T. and Pines, J., *Cell* 79:573–582, 1994). Thus this 5'ALT sequence most likely represents an untranslated ORF that plays a role in the complex regulation of these cell cycle inhibitors. The presence of abundant alternative transcripts for p16 and p15 may provide an explanation for certain issues regarding their role as tumor suppressor genes. The absence of p15 and p16 point mutations in many primary tumors may reflect their complex genomic organization and regulation in the 9p21 region, perhaps resulting in strong selection for alternative mechanisms of inactivation in human cancers.

Although the invention has been described with reference to the presently preferred embodiment, it should be understood that various modifications can be made without departing from the spirit of the invention. Accordingly, the invention is limited only by the following claims.

We claim:

1. A method for detecting the presence or absence of human chromosome 9p21 or fragments thereof comprising contacting a sample containing human chromosomal DNA with a polynucleotide of FIG. 1a (SEQ ID NO:1), and detecting the hybridization of the chromosomal DNA with the polynucleotide of FIG. 1a (SEQ ID NO: 1).

2. The method of claim 1, wherein the reagent is a polynucleotide.

3. A method for detecting a cell proliferative disorder in a tissue of a subject comprising contacting a target cellular component of the tissue with a reagent which detects a 5'ALT mediated alternate p16 transcript or truncated p16 polypeptide and detecting said alternate transcript or truncated polypeptide, wherein the alteration is indicative of a cell proliferative disorder.

4. The method of claim 3 wherein the tissue is selected from prostate, breast, colon, lung and renal tissue.

5. The method of claim 3, wherein the target cellular component is a nucleic acid.

6. The method of claim 5, wherein the nucleic acid is DNA.

7. The method of claim 6, wherein the DNA is a promoter region.

8. The method of claim 3, wherein the reagent is a probe.

9. The method of claim 8, wherein the probe is nucleic acid.

10. The method of claim 8, wherein the probe is detectably labeled.

11. The method of claim 10, wherein the label is selected from the group consisting of a radioisotope, a bioluminescent compound, a chemiluminescent compound, a fluorescent compound, a metal chelate, or an enzyme.

12. The method of claim 3, herein the reagent is a restriction endonuclease.

13. The method of claim 12, wherein the restriction endonuclease is methylation sensitive.

14. The method of claim 13, wherein the restriction endonuclease is selected from the group consisting of SmaI, SacII, EagI, MspI, HpaII and BssHII.

15. The method of claim 5, wherein the nucleic acid is amplified prior to contacting with a reagent.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 780 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TCCCGAGGCA  GTTATGTGAA  ATATGGCCTC  GATCTTGGAG  GTCCGGGTGG  GAGTGGGGGT      60

GGGGTGGGGG  TGGGGGTGAA  GGTGGGGGGC  GGGCGCGCTC  AGGGAAGGCG  GGTGCGCGCC     120
```

-continued

| | | | | | | |
|---|---|---|---|---|---|---|
| TGCGGGGCGG | AGATGGGCAG | GGGGCGGTGC | GTGGGTCCCA | GTCTGCAGTT | AAGGGGGCAG | 180 |
| GAGTGGCGCT | GCTCACCTCT | GGTGCCAAAG | GGCGGCGCAG | CGGCTGCCGA | GCTCGGCCCT | 240 |
| GGAGGCGGCG | AGAACATGGT | GCGCAGGTTC | TTGGTGACCC | TCCGGATTCG | GCGCGCGTGC | 300 |
| GGCCCGCCGC | GAGTGAGGGT | TTTCGTGGTT | CACATCCCGC | GGCTCACGGG | GGAGTGGGCA | 360 |
| GCGCCAGGGG | CGCCCGCCGC | TGTGGCCCTC | GTGCTGATGC | TACTGAGGAG | CCAGCGTCTA | 420 |
| GGGCAGCAGC | CGCTTCCTAG | AAGACCAGGT | AGGAAAGGCC | CTCGAAAAGT | CCGGGGCGCA | 480 |
| CTTGTTTTGT | TTGGTGTGTG | ATTTCGTAAA | CAGATAATTC | GTCTCTAGCC | CATTCTAGGA | 540 |
| GGAGGAGGAG | ATAACCGCGG | TGGAGGCTTC | CCATTCGGGT | TACAACGACT | TAGACATGTG | 600 |
| GTTCTCGCAG | TACCATTGAA | CCTGGACCTC | CCTTCACACA | GCCCTCAATC | GTGGGAAACT | 660 |
| GAGGCGAACA | GAGCTTCTAA | ACCCACCTCA | GAAGTCAGTG | AGTCCCGAAT | ATCCTGGGTG | 720 |
| GGAATGACTA | AGACACACAC | ACACACACAC | ACACACACAC | ACACACACAG | TAGGAAATGT | 780 |

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCCGAGGTT TCTCAGAG                                                  18

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:3:

CAUCAUCAUC AUGATGTCGC ACGGTACCTG                          30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:4:

CUACUACUAC UAACGGGTCG GGTGAGAGTG                          30

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
AGTGGCGCTG CTCACCTC                                                              18
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
TCCCGAGGTT TCTCAGAG                                                              18
```

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GGGTGGGAAA TTGGGTAAG                                                             19
```

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
GGGTCACCAA GAACCTGC                                                              18
```

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TCCCAGTCTG CAGTTAAGG                                                             19
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GTCTAAGTCG TTGTAACCC G                                                           20
```

( 2 ) INFORMATION FOR SEQ ID NO:11:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

AGTGCATCAG CACGAGGG  18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AACATGGTGC GCAGGTTC  18

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CGCCGAGCGC ACGCGGTCCG CCCC  24

( 2 ) INFORMATION FOR SEQ ID NO:14:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GGATCCTAAT ACGACTCACT ATAGGGAGAC CACCATGGCG CTGCTCACCT CTGGTG  56

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TGGAGCCTTC GGCTGAC  17

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TCATGATGAT GGGCAGCG                                                                                              18

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGGACCTTCC GCGGCAT                                                                                               17

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TCCCGAGGTT TCTCAGAG                                                                                              18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TCCCAGAATG CCAGAGGC                                                                                              18

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AGTACACGAC ACTGACGAAC                                                                                            20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear -continued (ii) MOLECULE TYPE: DNA (genomic)

(xi) SEQUENCE DESCRIPTION: SEQ ID NO:21:

GCGCTACCTG ATTCCAATTC 20